US010168335B2

United States Patent
Lohse et al.

(10) Patent No.: US 10,168,335 B2
(45) Date of Patent: *Jan. 1, 2019

(54) RAPID AND SENSITIVE METHOD FOR DETECTION OF BIOLOGICAL TARGETS

(71) Applicant: Dako Denmark A/S, Glostrop (DK)

(72) Inventors: Jesper Lohse, Herlev (DK); Kenneth Heesche Petersen, Smorum (DK)

(73) Assignee: DAKO DENMARK A/S, Glostrup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/165,823

(22) Filed: May 26, 2016

(65) Prior Publication Data

US 2016/0370375 A1    Dec. 22, 2016

Related U.S. Application Data

(62) Division of application No. 12/678,937, filed as application No. PCT/DK2008/000327 on Sep. 16, 2008, now Pat. No. 9,377,465.

(Continued)

(51) Int. Cl.
   *G01N 33/58* (2006.01)
   *C12Q 1/28* (2006.01)
   (Continued)

(52) U.S. Cl.
   CPC ........... *G01N 33/581* (2013.01); *C12Q 1/28* (2013.01); *C12Q 1/6806* (2013.01); *G01N 2333/908* (2013.01)

(58) Field of Classification Search
   CPC .................. G01N 33/581; C12Q 1/28
   See application file for complete search history.

(56) References Cited

U.S. PATENT DOCUMENTS

5,196,306 A    3/1993    Bobrow et al.
5,583,001 A    12/1996   Bobrow et al.
(Continued)

FOREIGN PATENT DOCUMENTS

EP    0 436 597 B1    4/1997
EP    0 623 679 B1    6/2003
(Continued)

OTHER PUBLICATIONS

Piris, J. et al., "An Imunoperoxidase Technique for the Identification of Gastrin Producing Cells," *J. Clin. Path.*, 27:798-799 (1974).
(Continued)

*Primary Examiner* — Shafiqul Haq

(57) ABSTRACT

The present invention relates to a method of biological labeling that occurs via a free radical chain reaction. The labeling occurs due to deposition of a detectable reporter molecule from a media comprising a substance comprising at least two moieties of a peroxidase enzyme substrate (termed herein 'cross-linker') in a target site comprising peroxidase activity and a biological marker. The labeling reaction described herein may generally be used to detect targets in a host of experimental schemes for detecting and visualizing a biological or chemical target, including immunohistochemistry (IHC), in situ hybridization (ISH), antibody-based staining methods such as ELISA, Southern, Northern, and Western blotting, and others.

12 Claims, 3 Drawing Sheets

Related U.S. Application Data

(60) Provisional application No. 60/994,206, filed on Sep. 18, 2007.

(51) Int. Cl.
*C12Q 1/68* (2018.01)
*C12Q 1/6806* (2018.01)

(56) References Cited

U.S. PATENT DOCUMENTS

| | | | |
|---|---|---|---|
| 5,585,089 | A | 12/1996 | Queen et al. |
| 5,688,966 | A | 11/1997 | Bobrow et al. |
| 5,731,158 | A | 3/1998 | Bobrow et al. |
| 5,767,287 | A | 6/1998 | Bobrow et al. |
| 5,863,748 | A | 1/1999 | Bobrow |
| 6,372,937 | B1 | 4/2002 | Bobrow et al. |
| 6,593,100 | B2 | 7/2003 | Bobrow et al. |
| 7,183,072 | B1 | 2/2007 | Hainfeld |
| 7,252,955 | B2 | 8/2007 | Pant et al. |
| 8,435,735 | B2 * | 5/2013 | Lohse ............ C08G 63/672 435/6.1 |
| 9,091,691 | B2 * | 7/2015 | Lohse ............ G01N 33/581 |
| 2012/0270242 | A1 | 10/2012 | Lohse |

FOREIGN PATENT DOCUMENTS

| | | |
|---|---|---|
| EP | 0 368 684 B2 | 9/2004 |
| EP | 0 589 877 B2 | 10/2005 |
| WO | WO 99/43846 | 9/1999 |
| WO | WO 03/002733 A2 | 1/2003 |
| WO | WO 2007/015168 A3 | 2/2007 |

OTHER PUBLICATIONS

Figueroa-Espinoza, M. et al., "Oxidative Cross-Linking of Pentosans by a Fungal Laccase and Horseradish Peroxidase: Mechanism of Linkage Between Feruloylated Arabinoxylans," *Cereal Chem.*, 75:259-265, (1998).

Lipkowski, P. et al., "The Synthesis and Structure of Diaza-and Tetraazacoronands," *Pol.J. Chem.*, 76:729-736, (2002).

Lohse, A. et al., "Solid-Phase Oligosaccharide Tagging (SPOT): Validation on Glycolipid-Derived Structures," *Ang. Chemie*, 45:4167-4172, (2006).

Caldwell, J. et al., "ABTS: A Safe Alternative to DAB for the Enhancement of Blood Fingerprints," *J. Forensic Sci.*, 45:785-794, (2000).

Good, N. et al., "Hydrogen Ion Buffers for Biological Research," *Biochemistry*, 5(2):467-477, (1966).

Shi, S. et al., "Antigen Retrieval Immunohistochemistry: Past, Present and Future," *J. Histochem. & Cytochem.*, 45(3):327-343, (1997).

Kohler, G. et al., "Continuous Cultures of Fused Cells Secreting Antibody of Predefined Specificity," *Nature*, 256:495-497, (1975).

McCafferty, J., et al., "Phage Antibodies: Filamentous Phage Displaying Antibody Variable Domains," *Nature*, 348:552-554, (1990).

Kang, S., et al,. "Linkage of Recognition and Replication Functions by Assembling combinatorial Antibody Fab Libraries along Phage Surfaces," *Proc. Natl. Acad. Sci.*, 88:4363-4366, (1991).

Marks, J., et al., "By-Passing Immunization• Building High Affinity Human Antibodies by chain Shuffling," *Bio/Tech.*, 10:779-783, (1992).

Waterhouse, P. et al., "Combinatorial Infection and in Vivo Recombination: A Strategy for Making Large Phage Antibody Repertoires," *Nucleic Acids Reas.* 21(9):2265-2266, (1993).

Jones, R. "Cancer Risk Assessments in Light of Chernobyl," *Nature*, 323:585-586, (1986).

Nielson, P. "Peptide Nucleic Acid: A Versatile Tool in Genetic Diagnostics and Molecular Biology," Curr Opin Biotech. 12:16-20 (2001).

Sorensen, M., et al., "Functionalized LNA (locked nucleic acid): High-Affinity Hybridization of Oligonucleotides Containing N-Acylated and N-Alkylated 2'-Amino-LNA Monomers," Chem. Commun., 2130-2131, (2003).

Altschul, S., et al., "Gapped BLAST and PSI-BLAST: A new Generation of Protein Database Search Programs," *Nucleic Acids Reas.*, 25(17):3389-3402, (1997).

International Search Report dated Jun. 17, 2009, for International Application No. PCT/DK2008/000327.

Odinot et al. (1998) In situ localisation of Yersinia enterocolitica by catalysed reporter deposition signal amplification. Journal of Clinical Pathology 51:444-449.

Speel et al. (1999) Amplification methods to increase the sensitivity of in situ hybridization-Play CARD(S). The Journal of Histochemistry & Cytochemistry 47(3):281-288.

* cited by examiner

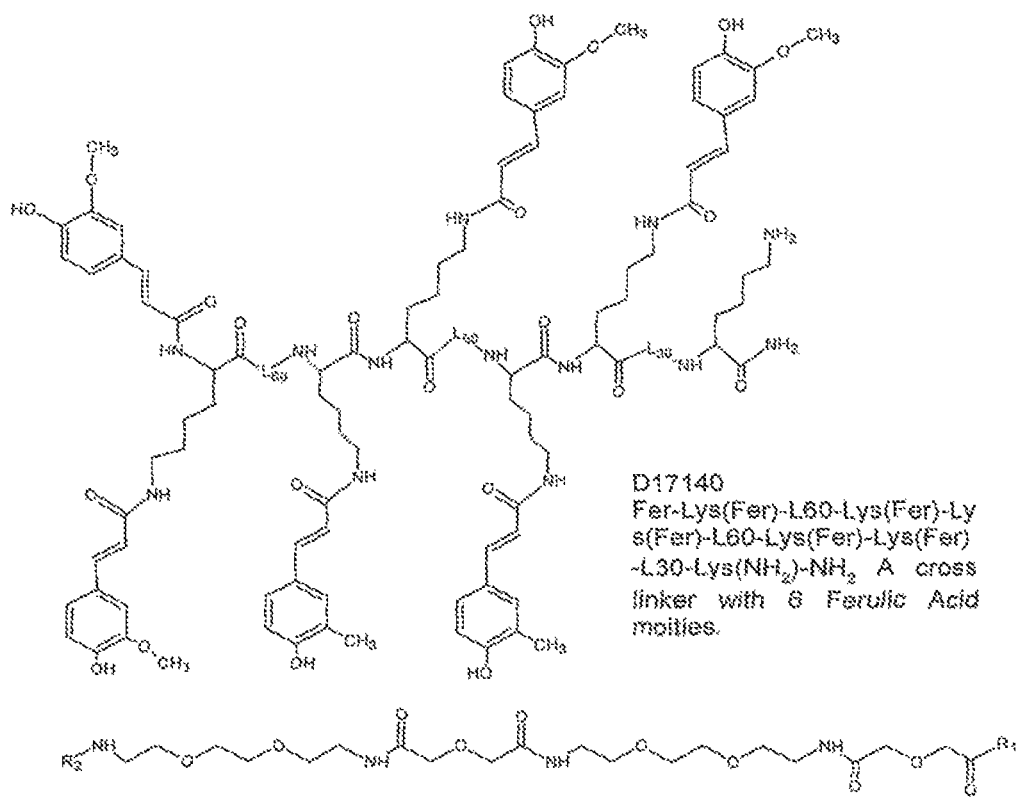
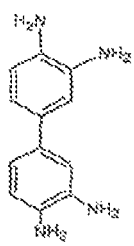
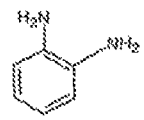
Figure 1

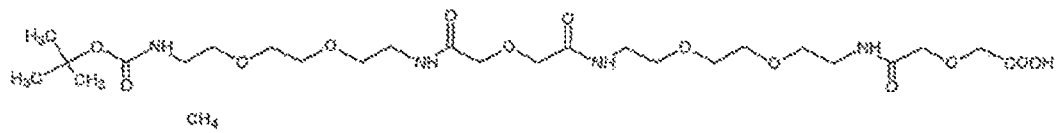

29-Boc-Amino-(3,9,12,18,24,27-hexaoxa)-(6,15,21-triaza)-(5,16,20-trioxo)-Nonacosanoic Acid "Boc-L30-OH", the monomer used to synthesize the linkers and conjugates.

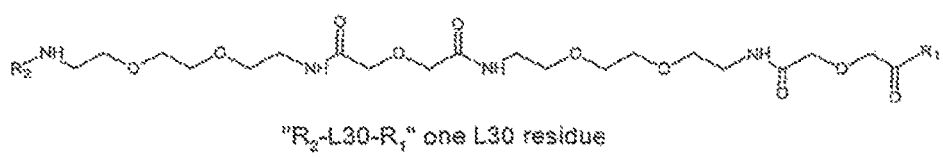

"R$_2$-L30-R$_1$" one L30 residue

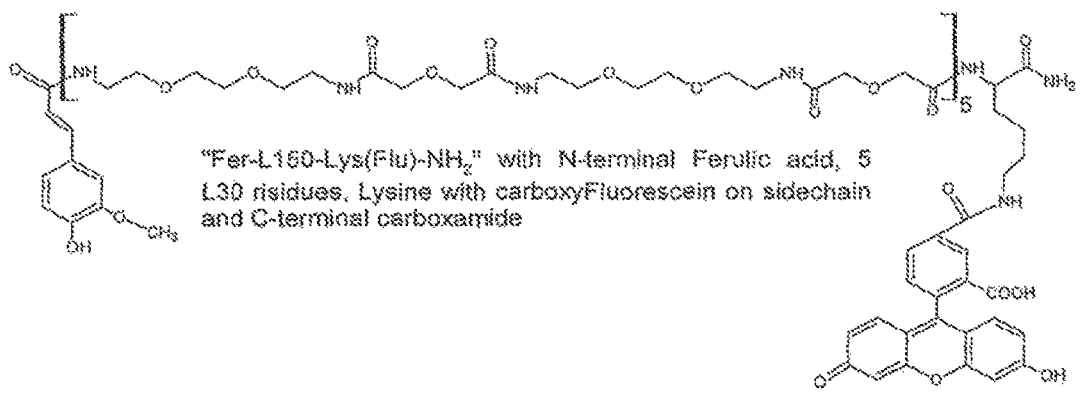

"Fer-L150-Lys(Flu)-NH$_2$" with N-terminal Ferulic acid, 5 L30 residues, Lysine with carboxyFluorescein on sidechain and C-terminal carboxamide

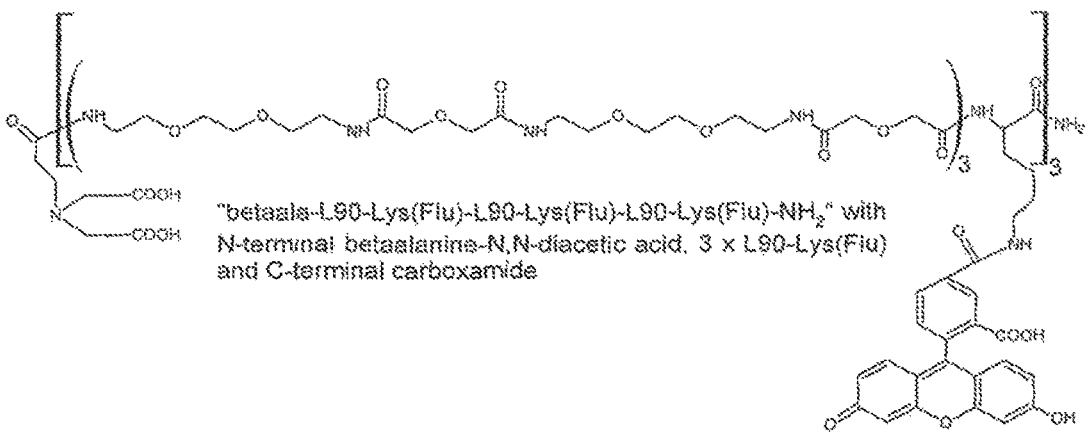

"betaala-L90-Lys(Flu)-L90-Lys(Flu)-L90-Lys(Flu)-NH$_2$" with N-terminal betaalanine-N,N-diacetic acid, 3 × L90-Lys(Flu) and C-terminal carboxamide

Figure 2

RAPID AND SENSITIVE METHOD FOR DETECTION OF BIOLOGICAL TARGETS

PRIORITY CLAIM

This application is a continuation of U.S. application Ser. No. 12/678,937, filed Jul. 12, 2010, which is a national stage filing under 35 U.S.C. § 371 of International Application No. PCT/DK2008/000327, filed Sep. 16, 2008, and designating the United States of America, which claims benefit of the filing date of and right of priority to U.S. Provisional Application No. 60/994,206, filed Sep. 18, 2007, the contents of which are incorporated herein by reference.

FIELD OF THE INVENTION

The present invention relates to a method of biological labeling that occurs via a free radical chain reaction. The labeling reaction described herein may generally be used to detect targets in a host of experimental schemes for detecting and visualizing a biological or chemical target, including immunohistochemistry (IHC), in situ hybridization (ISH), antibody-based staining methods such as ELISA, Southern, Northern, and Western blotting, and others.

BACKGROUND

Detection of biological or chemical targets in a sample using a detectable label is a procedure at the heart of many biological diagnosis and detection methods. In some cases the target may be a particular polynucleotide sequence or gene, a mutation of a gene, a genetic expression pattern, detected at the DNA or RNA level, either in situ or after extraction or isolation. In other cases, the target may be a peptide, protein, antigen, or other substance, again detected in situ or after isolation or laboratory manipulation. The target may also be a particle or debris of organic origin.

Many standard detection methods, e.g. IHC, ISH, ELISA or blotting, employ labeling schemes to detect the desired targets. Typically, those schemes involve incubating an experimental sample potentially containing the detectable target with a probe, and then detecting the binding between probe and target with a detectable label which may give off a color, a fluorescent signal, or radioactivity, for example. One or many probe molecules may bind to each target, depending upon the specifics of the scheme used. In some cases, especially when the target is present in low concentration, it is necessary to amplify the signal from the target-probe binding by adding one or more amplification layers to the system. For example, if the probe is a primary antibody that recognizes the target, a secondary antibody that recognizes the primary antibody probe may be added such that many secondary antibodies bind to each primary antibody. If the secondary antibodies are attached to a detectable label such as a fluorophore or chromophore, then, via amplification, each target molecule in the sample may effectively be bound to multiple fluorophores or chromophores instead of only one or a few fluorophores or chromophores. Hence, the target will produce a stronger detection signal after amplification.

Some detection experiments, however, have a tendency to produce relatively diffuse-looking signals, especially if the sample is allowed to rest for a period of time before analysis. For example, the one or more probes and/or detectable labels bound to a target may slowly diffuse away from the target, or away from each other over time. In some cases buffer changes that affect the binding affinity of the target, probe, and amplification layers can also cause signal diffusion. Many detectable labels are bound to targets by non-covalent interactions such as protein-ligand binding or polynucleotide hybridization. Buffer changes after labeling may reduce the affinity between the target, probe, and detectable label, causing the various components to dissociate. Simple diffusion over a period of time, such as several days, may also cause dissociation between target, probe, and detectable label, rendering the signal diffuse.

Prior art describes only a very few techniques which allow to overcome the above mentioned problems, but yet only partially. One example of such techniques is a method of catalyzed reporter deposition (CARD) described in U.S. Pat. No. 5,863,748; 5,688,966; 5,767,287; 5,731,158; 5,583,001, 5,196,306, 6,372,937 or 6,593,100. This method utilizes so-called "analyte-dependent enzyme activation system" (ADEAS) to catalyze the deposition of a detectable label onto the solid phase of an assay platform. In the assay format, an enzyme comprised by the ADEAS reacts with a conjugate consisting of a detectably labeled substrate specific for the enzyme. When the enzyme and the conjugate react, an activated conjugate is formed which deposits covalently at a site where a specific receptor for the activated conjugate is immobilized. Thus, because of the conjugate comprises a label it plays a role of a reporter which indicates the presence of a target in the site. Enzymatically deposited labels may be detected directly or indirectly. The method results in signal amplification and improved detection limits.

The CARD method may be used in assay formats, where the target to be detected is a receptor immobilized on a solid support, e.g. a membrane. Such assays formats include sandwich immunoassays and membrane based nucleic acid hybridization assays. The CARD method is also applicable to detection of biological targets e.g. by immunohystochemistry (IHC), as described in U.S. Pat. No. 6,593,100. The method described in U.S. Pat. No. 6,593,100 utilizes a reaction of horse radish peroxidase (HRP) with a labeled conjugate comprising a HRP substrate in the presence of an enhancer. Both HRP substrate and enhancer are derivatives of phenol. Upon reaction with HRP the HRP substrate becomes activated and binds to receptor sites of the sample, e.g. proteins.

Despite of having some advantageous features, e.g. an increased sensitivity of detection, the method is limited to reporter molecules which are labeled HRP substrates selected either from tyramide or p-hydroxycinnamic acid or derivatives thereof.

The present invention overcomes the limitations of the above described CARD method and provides a novel method for a rapid and sensitive detection of biological and chemical markers. The method comprises both valuable features of the CARD method and new features that make it applicable to a wider range of the assay formats and independent from a narrow selection of reporter molecules and allow a rapid, precise and sensitive detection of a variety of biological or chemical targets.

SUMMARY OF INVENTION

The present invention is based on finding that a variety of molecules can be deposited from a solution that comprises a substance comprising at least two moieties of a peroxidase enzyme substrate (termed herein "cross-linker") in a site comprising a peroxidase activity, e.g. in a site comprising a moiety of a peroxidase enzyme, e.g. HRP. The depositing molecule may be a detectable molecule, e.g. a molecule that itself may give off a color, a fluorescent signal, or radioactivity or that comprises a detectable label which may give off a color, a fluorescent signal, or radioactivity, accordingly, the site of deposition of this detectable molecule can be detected, and if the deposition site comprises a biological or chemical marker, the presence of this biological or chemical marker can be detected as well. The depositing molecule will thus "report" the presence of the biological marker in the site of its deposition. Accordingly, such detectable depositing molecules are termed herein "reporters".

One possible reason for the reporter molecule is deposited from a media comprising the cross-linker in the presence of peroxidase activity is that a free-radical chain reaction initiated by the reaction between the peroxidase and the cross-linker is taking place in the media. Free radicals of the cross-linker molecules formed in the course of this reaction may prime reporter molecules present in the same media; the primed reporter molecules may further react to each other and form large insoluble aggregates which are deposited in or around the sites comprising peroxidase activity (termed herein "target sites"). Because of the peroxidase activity is strictly localized to target sites, the result of this chain reaction is that the reporter molecules are deposited only in the target sites or in a very close proximity to these sites. If such target sites comprise a biological or chemical marker, e.g. a protein or nucleic acid, the marker may thus be detected by detecting the deposited reporter.

It was surprisingly found that molecules comprising at least two moieties of a peroxidase enzyme substrate can play a role of cross-linker in the method of the invention. Accordingly, the term "cross-linker" is used herein to designate a molecule which comprises at least two moieties of a molecule (or at least two moieties of two different molecules) which can serve as substrate of a peroxidase (the term "peroxidase" is interchangeably used herein with the term "peroxidase enzyme" or "peroxidase activity"), and which is capable of cross-linking activity when activated by the peroxidase. The cross-linkers of the present invention are capable of cross-linking of at least two reporter molecules.

It was found that deposition of the reporter mediated by the reaction of a cross-linker and peroxidase is very rapid and site-directed, i.e. the reporter is deposited non-randomly but specifically in a target site which comprises peroxidase activity, e.g. a moiety of HRP. The deposited reporter is tightly attached to the target site and does not diffuse from the site over time. Accordingly, a signal associated with the deposited reporter is precisely localized and stays sharp over time.

Accordingly, a first aspect of the invention is a method for the target site-directed deposition of a reporter, wherein said method comprising incubating a target site in a medium comprising a reporter and a cross-linker, wherein said target site comprises a peroxidase activity, wherein said reporter is a detectable molecule, and wherein said cross-linker is a molecule comprising at least two moieties of a peroxidase enzyme substrate.

Another aspect of the invention relates to a media for the site-directed reporter deposition, wherein said media is a water buffered solution having pH from about 4 to about 9, comprising $10^{-5}$-$10^{-2}$M a cross-linker comprising at least two moieties of a peroxidase substrate,
0.1-10 mM a peroxide compound,
0-20% an organic modifier, and
0-2 M a salt.

Another aspect of the invention relates to a method of detection of a biological marker in a sample in vitro, wherein said method comprises a step of site-directed deposition of a reporter described herein. The method may advantageously be used as in manual as in automated procedures for the detection of biological markers. In particular, the invention The method of detecting a biological marker in a biological sample in vitro according to the invention comprises the following steps:

a) incubating a sample presumably comprising a biological marker with one or more probes, wherein the least one of said one or more probes comprises at least one moiety of horse radish peroxidase (HRP), thereby forming a complex of the biological marker with the at least one probe comprising at least one moiety of HRP, i.e. forming a target site;

b) incubating the sample comprising the complex of the biological marker with the at least one probe comprising at least one moiety of HRP of step (a), i.e. the sample comprising a target site, in a media comprising a reporter and a cross-linker, thereby depositing the reporter in the target site, i.e. the site where the complex of (a) is present;

c) detecting the deposited reporter of (b) and thereby detecting the biological marker.

Further aspect of the invention relates to a cross-linker molecule which can be advantageously used for the site-directed deposition of a reporter, wherein said molecule has the following formula:

(R1)n-(X)q-R2(m), wherein

R1 and R2 are moieties of a peroxidase enzyme substrate, X is a linker grouping of the following formula

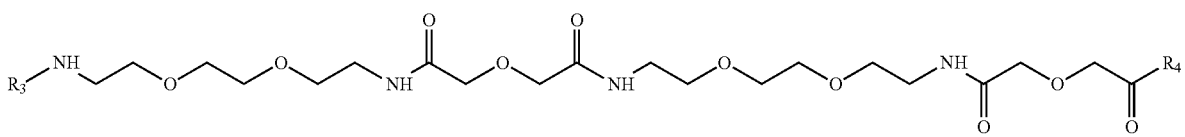

wherein R3 and R4 are residues of amino acid lysine, and m, n and q are integers from 1 to 10.

DESCRIPTION OF THE DRAWINGS

FIG. 1 shows examples of the cross-linker molecules of the invention.

FIG. 2 shows examples of the reporter molecules of the invention.

FIG. 3(1) shows incubating a sample with a first probe 1 (1P1) e.g. an HRP-conjugated antibody). FIG. 3(2) shows incubating the sample of FIG. 3 (1 with reporter 1 (R1) (e.g. a ferulic acid-PNA1 conjugate) in the presence of a cross-linker (e.g. DAB). FIG. 3(3) shows incubating the sample of FIG. 3(2) with hydrogen peroxide (e.g. at >3% v/v which quenches the residual HRP activity as shown b the X over the HRP at the A1 site in FIG. 3(4). FIG. 3(4) shows incubating the sample of FIG. 3(3) with first probe 2 (1P2) (e.g. HRP-conjugated antibody AB2). The first part of FIG. 3(5) shows incubating the sample FIG. 3(4) with reporter 2 (R2) (e.g. ferulic acid-PNA2 conjugate) and DAB, resulting in the deposition of report 2 at the A2 site, as shown in the second part of FIG. 3(5). The first part of FIG. 3(6) shows incubating the sample shown in the second part of FIG. 3(5) with second probe 1 (2P1) (e.g. PNA1'-FITC) and with second probe 2 (2P2) (e.g. PNA2'-Texas Red), with the results shown in the second part of FIG. 3(6). That is the second part of FIG. 3(6) shows an example of when a green fluorescent signal (emanating from PNA1'-FITC) may be detected from the target site where R1 is deposited, a red fluorescent signal (emanating from PNA2'-Texas Red) may be detected from the target site of R2 deposition, resulting in a yellow signal where both R1 and R2 are deposited, i.e., from the site were both targets A1 and A2 are present, as shown in the second part of FIG. 3(6).

DETAILED DESCRIPTION OF INVENTION

Figure 3:
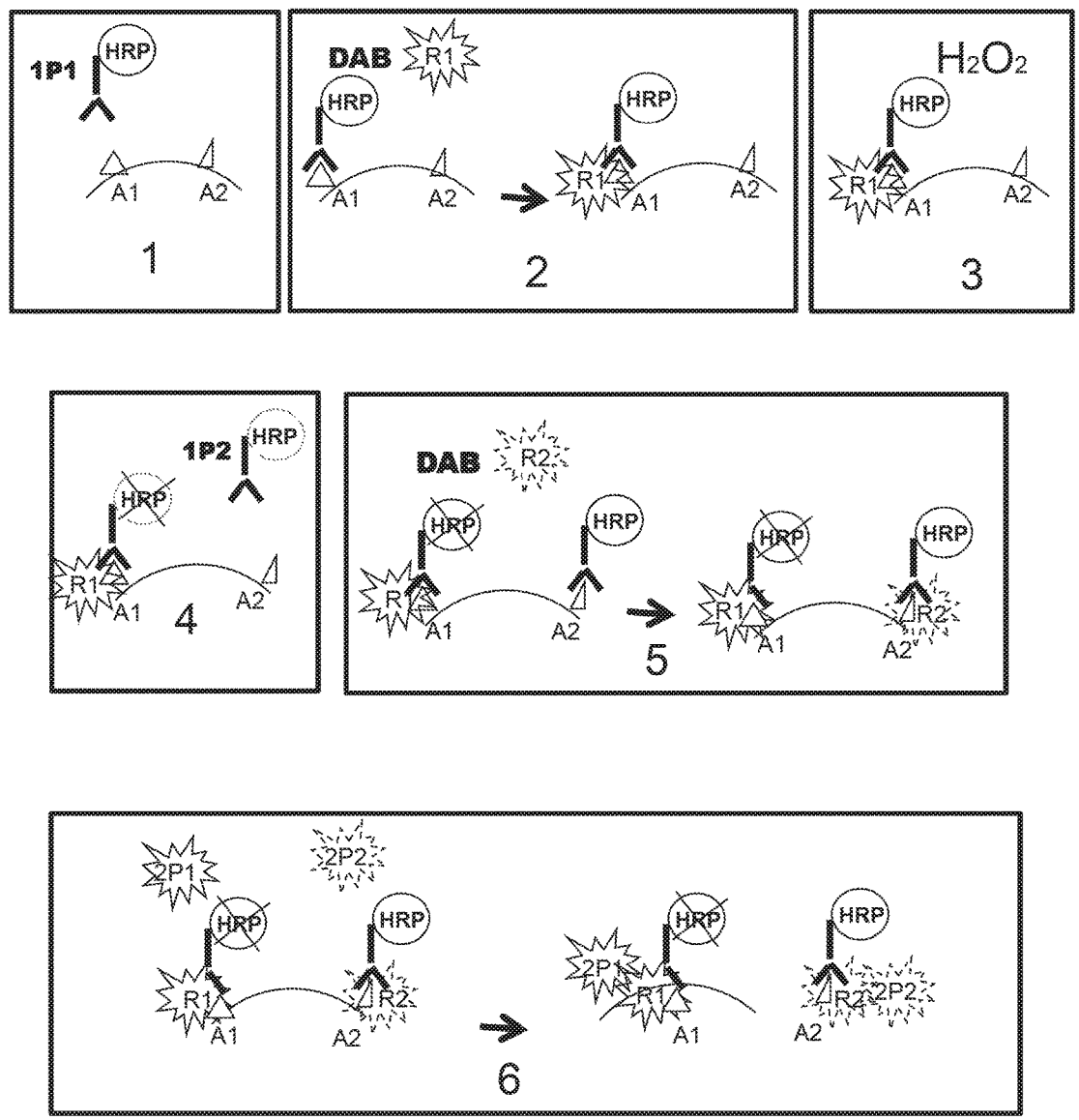
FIG. 3 shows a schematic presentation of the method of detection of a biological marker of the invention applied for the detection of two different markers.

1. Method of Site-Directed Deposition of a Reporter

In one aspect the present invention relates to a method of deposition of a reporter in a target site, said method comprising incubating a target site in a medium comprising a reporter and a cross-linker, wherein said target site comprises a peroxidase activity, wherein said reporter is a detectable molecule, and wherein said cross-linker is a molecule comprising at least two moieties of a peroxidase enzyme substrate.

Cross-Linker

The term "cross-linker" is used herein to refer to a molecule capable of linking together at least two molecules, e.g. at least two reporter molecules. The cross-linker of the invention comprises at least two moieties of a peroxidase enzyme substrate, wherein said two moieties may be bound to each other by a chemical bond, or may be liked via a linking molecule or grouping.

Accordingly, the invention relates to a cross-linker which a compound of the following formula:

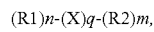

wherein
R1 and R2 are moieties of a peroxidase enzyme substrate
X is a linker grouping or a chemical bond, and
m, n and q are integers from 1 to 10.

In one embodiment the cross-linker of the invention may be a compound of the following formula:

$$R1)n\text{-}(X)q\text{-}R2(m),$$

wherein R1 and R2 are moieties of a peroxidase enzyme substrate,
X is a chemical bond, and
m, n and q are integers selected from 1 to 10.

One non-limiting example of such cross-linker, e.g. wherein X is a covalent bond and each of m, n, and q is 1, may be 3,3 diaminobenzidine (DAB). DAB comprises two moieties of horse radish peroxidase (HRP) substrate o-phenylenediamine (OPD) (i.e. R1 and R2 are the OPD moieties) which are linked to each other via one covalent bond.

In another embodiment, the invention relates to a cross-linker of the formula:

$$(R1)n\text{-}(X)q\text{-}(R2)m,$$

wherein R1 and R2 are moieties of a peroxidase enzyme substrate, X is a linking molecule or a linking grouping, and m, n and q are integers from 1 to 10.

In such cross-linker the (X) grouping may be any linker molecule or linking grouping. In one preferred embodiment X may be a linking grouping of the formula:

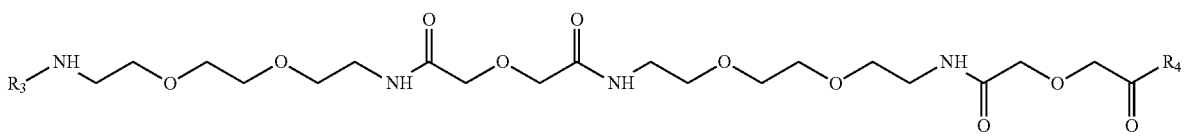

wherein R3 and R4 are residues of amino acid lysine. Such linker grouping is termed herein L30.

In some embodiments the cross-linkers may comprise many moieties of a peroxidase substrate (n and/or m more than 2) and several moieties of the linking molecule X (i.e. q>1). In other embodiments linkers may comprise a fewer moieties of a peroxidase substrate (each of n and ni are 1) and several moieties of the linking molecule X (i.e. q>1).

In some embodiments the cross linker may be a compound in which several moieties of a peroxidase substrate bound directly to each other via chemical bonds. The moieties R1 and R2 may in one embodiment be moieties of the same peroxidase enzyme substrate. In another embodiment R1 and R2 may be moieties of two or more different peroxidase enzyme substrates.

An example of a cross-linker, wherein the linking grouping (X) is represented by a dimer of the L30 linker and R1 and R2 are multiple moieties of a HRP substrate may be compound D17140 which is demonstrated in FIG. 1 and described in Example 1.8. Another example of the cross-linker of the invention may be compound D17120 described in Example 1.5. The molecule of D17140 comprises 6 moieties of HRP substrate ferulic acid attached through lysine residues to a polymer made of several moieties of L30. The molecule of D17120 also comprises 6 moieties of ferulic acid attached to another L30 polymer.

By varying the number of peroxidase substrate moieties, linker grouping repeats and/or introducing charged moieties into cross-linker molecules, e.g. lysine residues such as in the D17140 molecule, it is possible to make cross-linkers with desirable features, e.g. cross-linkers having a good solubility in the media comprising a reporter.

Thus, in one preferred embodiment the cross-linker may be a molecule which comprises at least two moieties of a substrate of a peroxidase wherein bound to a each other via a covalent bond, in another preferred embodiment the cross-linker may be a molecule which comprises more than two moieties of a substrate of a peroxidase, wherein said moieties are linked together via one or more linking groupings.

In particular, in one preferred embodiment the moieties of the peroxidase substrate are moieties of o-phenylenediamine, in another preferred embodiment the moieties are the moieties of ferulic acid. In the latter embodiment it is preferred that the moieties of ferulic acid are linked together through one or more molecules of the L30 linker.

Reporter

The term "reporter" is used herein to refer to any detectable molecule, wherein the detectable molecule is a molecule selected from a molecule which can give off a color, a fluorescent signal, or radioactivity, or it is a member of a specific binding pair, or it is a conjugate comprising a detectable moiety, such as chromogenic, fluorescent, chemiluminescent, radioactive label, enzyme moiety, enzyme substrate, detectable particle, etc., or it is a molecule, which can be deposited form the media comprising a cross-linker (embodiments of the cross-linker are described above) in the presence of peroxidase activity and labeled as deposited.

A substance which has the cross-linking capability according to the invention may in one embodiment be used either as crosslink-linker or reporter; however, one and the same molecule may not be used in the same embodiment both as cross-linker and reporter.

A cross-linker of the formula (R1)n-(X)q-(R2)m,
wherein R1 and R2 are moieties of o-phenylenediamine,
X is a covalent bond, and
m, n and q are 1, may not be used as reporter in any embodiments of the invention.

Non-limiting examples of molecules that may be used as a cross-linker in one embodiment and reporter in another embodiment are the molecules 017120 and D17140 described above (see also in Examples 1.1 to 1.8.).

The reporter molecule according to the invention is a molecule which is soluble in the media comprising a cross-linker in the absence of peroxidase activity. Concentration of the reporter in the media may vary from about $10^{-9}$ M to about $10^{-4}$ M, for example from about $10^{-9}$ M to about $10^{-8}$ M, such as from about $10^{-8}$ M to about $10^{-7}$ M, from about $10^{-7}$ M to about $10^{-8}$ M, or from about $10^{-8}$ M to about $10^{-8}$ M, or from about $10^{-8}$ M to about $10^{-4}$ M.

The reporter in one embodiment may be a detectable small molecule, e.g. selected from a fluorescent or chromogenic substance, hapten or enzyme substrate, or in another embodiment the reporter may be a large molecule, e.g. a conjugate comprising a backbone polymer and at least one detectable substance, wherein the detectable substance, i.e. detectable label, is attached to the backbone polymer via a chemical bond or via a linker molecule. Thus, the reporter may be a conjugate comprising two or more molecules, at least one of which is detectable, or the reporter may be a small molecule, such as a molecule which has the molecular mass that is not greater than 500-2000 Da, for example about 1000 Da. The reporter-conjugate may be a large molecule, typically a polymer molecule to which a detectable label is attached. The size of such reporter molecules may be very different and vary from $3\times10^3$ Da to $3\times10^6$ Da or more.

The reporter according to the invention may also be a molecule which is not "detectable". Such molecule cannot generate a signal which can be detected, e.g. by means for detection of color, fluorescence or radioactivity. Such reporter molecule can be detected when deposited by application of secondary means allowing the detection, e.g. detectable non-reporter molecules which can specifically bind to the deposited reporter. Such detection may comprise several steps on which one or more detectable substances will be applied to bind to this deposited "non-detectable" reporter molecule and thus make it visually detectable.

The reporter is a detectable molecule. It may be a small detectable molecule, or it may be a large detectable molecule. The small detectable molecule is typically a directly detectable molecule (some embodiments of small detectable molecules are described in this section and in the following sections below). The large detectable molecule is typically represented by a large, typically, not directly detectable molecule which is made detectable upon coupling this molecule to a small directly detectable molecule, or another detectable label. A large reporter molecule comprising a label is termed herein as "detectable conjugate". The detectable conjugate according to the invention may comprise two or more different molecules, at least one of which is a detectable label.

Both small detectable molecule and label comprised by a big reporter molecule may be selected from is a fluorescent, luminescent, bioluminescent, radioactive or chromogenic substance.

A number of fluorescent, luminescent, bioluminescent, radioactive or chromogenic labels may be used. Many of them are commercially available, for example fluorescent stains Alexa Fluors (Molecular Probes) and DyLight Fluors (Thermo Fisher Scientific). Other non-limited examples of labels and small reporter molecules may be the molecules of the group consisting of 5-(and 6)-carboxyfluorescein, 5- or 6-carboxyfluorescein, 6-(fluorescein)-5-(and 6)-carboxamido hexanoic acid, fluorescein isothiocyanate, rhodamine, tetramethylrhodamine, Cy2, Cy3, Cy5, AMCA, PerCP, R-phycoerythrin (RPE) allophycoerythrin (APC), Texas Red, Princeton Red, Green fluorescent protein (GFP) coated CdSe nanocrystallites, DNP, digoxiginin, ruthenium derivatives, luminol, isoluminol, acridinium esters, 1,2-dioxetanes and pyridopyridazines, radioactive isotopes of hydrogen, carbon, sulfur, iodide, cobalt, selenium, tritium, or phosphor.

In another embodiment a small detectable molecule or label may be a substance which is an enzyme substrate. An enzyme substrate may be selected form the group consisting of substrates of horse radish peroxidase (HRP), excluding DAB, alkaline phosphatase (AP), beta-galactosidase (GAL), glucose-6-phosphate dehydrogenase, beta-N-acetylglucosaminidase, p-glucuronidase, invertase, xanthine oxidase, firefly luciferase, glucose oxidase (GO). In one preferred embodiment the enzyme substrate label may be a HRP substrate, in another preferred embodiment the enzyme label may be an AP substrate.

Examples of useful substrates of HRP include 3-amino-9-ethylcarbazole (AEC), Benzidine dihydrochloride (BDHC), Hanker-Yates reagent (HYR), Indophane blue (IB), tetramethylbenzidine (TMB), 4-chloro-1-naphtol (CN), α-naphtol pyronin (α-NP), o-dianisidine (OD), 5-bromo-4-chloro-3-indolylphosphate (BCIP), Nitro blue tetrazolium (NBT), 2-(p-iodophenyl)-3-p-nitrophenyl-5-phenyl tetrazolium chloride (INT), tetranitro blue tetrazolium (TNBT), 5-bromo-4-chloro-3-indoxyl-beta-D-galactoside/ferro-ferricyanide (BCIG/FF), 5-amino-2-[3-[5-amino-1,3-dihydro-3,3-dimethyl-1-(4sulfobutyl)-2H indol-2-ylidene]-1-propenyl]-3,3dimethyl-1-(4sulfobutyl)-3H-Indolium. In one preferred embodiment the small molecule may be 5-amino-2-[3-[5-amino-1,3-dihydro-3,3-dimethyl-1-(4sulfobutyl)-2H-indol-2-ylidene]-1-propenyl]-3,3dimethyl-1-(4sulfobutyl)-3H-Indolium.

Examples of useful substrates of AP include Naphthol-AS-B1-phosphate/fast red TR (NABP/FR), Naphthol-AS-MX-phosphate/fast red TR (NAMP/FR), Naphthol-AS-B1-phosphate/fast red TR (NABP/FR), Naphthol-AS-MX-phosphate/fast red TR (NAMP/FR), Naphthol-AS-B1-phosphate/new fuschin (NABP/NF), bromochloroindolyl phosphate/nitroblue tetrazolium (BCIPINBT), 5-Bromo-4-chloro-3-indolyl-b-d-galactopyranoside (BCIG).

The label or a small reporter molecule may be an enzyme. Non-limiting examples of enzyme labels may be alkaline phosphatase (AP), beta-galactosidase (GAL), glucose-6-phosphate dehydrogenase, beta-N-acetylglucosaminidase, fl-glucuronidase, invertase, xanthine oxidase, firefly luciferase, glucose oxidase (GO) In one preferred embodiment the enzyme label is AP.

Yet, the detectable label of a conjugate reporter molecule or small reporter molecule may be a member of a specific binding pair. Members of specific binding pairs suitable for use in practicing the invention may be of the immune or non-immune type. Immune specific binding pairs are exemplified by antigen/antibody systems- or hapten/anti-hapten systems.

Haptens are small molecules thus permitting multiple copies to be attached to a single polymer molecule, in case the reporter comprises both a detectable label and polymer.

Haptens provide convenient target molecules for assay formats where it is necessary or advantageous to amplify a signal. Thus, the bound multiple copies of a hapten provide for enhanced sensitivity, e.g. increased signal strength. Examples of suitable haptens include FITC, DNP, myc Digoxigenin, nitrotyrosine biotin, avidin, strepavidin and anti-dye antibodies to e.g. tetramethylrhodamine, Texas Red, dansyl, Alexa Fluor 488, BODIPY FL, lucifer yellow and Alexa Fluor 405/Cascade Blue fluorophores.

The antibody member, whether polyclonal, monoclonal or an immunoreactive fragment thereof, of the binding pair can be produced by customary methods familiar to those skilled in the art. The terms immunoreactive antibody fragment or immunoreactive fragment mean fragments which contain the binding region of the antibody. Such fragments may be Fab-type fragments which are defined as fragments devoid of the Fc portion, e.g. Fab, Fab' and F(ab'), fragments, or may be so-called "half-molecule" fragments obtained by reductive cleavage of the disulfide bonds connecting the heavy chain components of the intact antibody. If the antigen member of the specific binding pair is not immunogenic, e.g. a hapten, it can be covalently coupled to a carrier protein to render it immunogenic.

Non-immune specific binding pairs include systems wherein the two components share a natural affinity for each other but are not antibodies. Exemplary non-immune binding pairs are biotin-avidin or biotin-streptavidin, folic acid-folate binding protein, complementary nucleic acids, receptor-ligand, etc. The invention also includes non-immune binding pairs which form a covalent bond with each other. Exemplary covalent binding pairs include sulfhydryl reactive groups such as maleimides and haloacetyl derivatives and amine reactive groups such as isothiocyanates, succinimidyl esters, sulfonyl halides, and coupler 20 dyes such as 3-methyl-2-benzothiazolinone hydrazone (MBTH) and 3-(dimethyl-amino)benzoic acid (DMAB), etc.

In some embodiments, it may be preferred that labels linked to a polymer molecule are different. In some embodiments it may be preferred to use a reporter that comprises two or more different labels. Any combination of different labels selected from any of the groups identified above may be made, e.g. a reporter may comprise a combination of a fluorescent label and enzyme label, a combination of a member of a specific binding pair, enzyme and/or enzyme substrate, etc.

If the reporter is represented by a conjugate of a polymer with one or more detectable molecules, in one embodiment the conjugate may comprise at least one polymer and at least one label, wherein the at least one label is linked to the at least one polymer via a chemical bond or via a linker groping, e.g. L30. Non-limited examples of such reporter are described in Examples, see for example Example 1.9. If the conjugate comprises more than one polymer, each of the polymers may be linked to one or more detectable labels.

The labels may be same or different. Different labels may be selected from any groups of the described above and used in any desired combinations.

Reporter Molecules Comprising Polymers

A large reporter molecule may comprise a polymer. The polymer comprised by a large reporter molecule may be any polymeric molecule. It may be soluble or insoluble in water on its own, but when serves as part of a reporter conjugate, it is soluble or can be made soluble in a water media or at least in the media of the invention described below. The polymer is preferably selected from molecules which can be deposited from the media comprising a cross-linker in the presence of peroxidase activity.

Examples of suitable polymers include polysaccharides such as dextrans, carboxy methyl dextran, dextran polyaldehyde, carboxymethyl dextran lactone, and cyclodextrins; pullulans, schizophyllan, scleroglucan, xanthan, gellan, O-ethylamino guaran, chitins and chitosans such as 6-O-carboxymethyl chitin and N-carboxymethyl chitosan; derivatized cellolosics such as carboxymethyl cellulose, carboxymethyl hydroxyethyl cellulose, hydroxyethyl cellulose, 6-amino-6-deoxy cellulose and O-ethylamine cellulose; hydroxylated starch, hydroxypropyl starch, hydroxyethyl starch, carrageenans, alginates, and agarose; synthetic polysaccharides such as ficoll and carboxymethylated ficoll; vinyl polymers including poly(acrylic acid), poly(acryl amides), poly(acrylic esters), poly(2-hydroxy ethyl methacrylate), poly(methyl methacrylate), poly(maleic acid), poly(maleic anhydride), poly(acrylamide), poly(ethyl-co-vinyl acetate), poly(methacrylic acid), poly(vinylalcohol), poly(vinyl alcohol-co-vinyl chloroacetate), aminated poly (vinyl alcohol), and co block polymers thereof; poly ethylene glycol (PEG) or polypropylene glycol or poly(ethylene oxide-co-propylene oxides) containing polymer backbones including linear, comb-shaped or hyperbranched polymers and dendrimers, including branched PAMAM-dendrimers; poly amino acids including polylysines, polyglutamic acid, polyurethanes, poly(ethylene imines), pluriol; proteins including albumins, immunoglobulins, and virus-like proteins (VLP), and polynucleotides, DNA, PNA, LNA, oligonucleotides and oligonucleotide dendrimer constructs. Also contemplated is the use of mixed polymers, i.e., a polymer comprised of one or more of the above examples including any of the polymers, the co-block polymers and random co-polymers.

The choice of polymer may depend on particular application where the method of the invention is used. Physical properties of the polymer may be selected depending on particular applications of the method to optimize the performance. Examples of these physical properties include the length and branching of the polymer. Furthermore, the polymer may carry various substituents. The substituents may be chemically protected and/or activated, allowing the polymer to be derivatized further. For example in one embodiment the polymer may be a nucleic acid, in another embodiment it may be a nucleic acid analog, in another embodiment it may be a polypeptide, in another embodiment it may be a polysaccharide, in other embodiments it may be any variant thereof.

By the term "nucleic acid" is meant a polymer composed of a chain(s) nucleotide monomers. The most common nucleic acids are deoxyribonucleic acid (DNA) and ribonucleic acid (RNA). A nucleotide is a compound that consists of a heterocyclic base (nucleobase), a sugar, and one or more phosphate groups. In the most common nucleotides the base is a derivative of purine or pyrimidine, and the sugar is the pentose (five-carbon sugar) deoxyribose or ribose. As said, nucleotides are the monomers of nucleic acids. The nucleobases are the parts of nucleotide that may be involved in pairing in RNA and DNA molecules. The nucleobases include cytosine, guanine, adenine, thymine (DNA), uracil (RNA).

By the term "nucleic acid analog" is meant a polymer, which is a homopolymer composed of nucleotide monomers, wherein nucleobases may be natural, modified and/or synthetic, or which is a heteropolymer composed of monomers of natural, modified and synthetic nucleobases, amino acids and other types of monomers. "Home-" and "hetero-" in respect of a polymer indicates that the polymer is composed of monomer of different chemical origin, e.g. a polymer composed of nucleobase monomers only is a homopolymer, a polymer composed of nucleobase and amino acid monomers is heteropolymer. An example of a homopolymer may be a DNA or RNA molecule, an example of a heteropolymer may be a PNA molecule. Peptide nucleic acid (PNA) is a chemical similar to DNA or RNA. PNA is artificially synthesized compound. DNA and RNA have a deoxyribose and ribose sugar backbone, respectively, whereas PNA's backbone is composed of repeating N-(2-aminoethyl)-glycine units linked by peptide bonds. The various purine and pyrimidine bases are linked to the backbone by methylene carbonyl bonds. PNAs are depicted like peptides, with the N-terminus at the first (left) position and the C-terminus at the right. Since the backbone of PNA contains no charged phosphate groups, the binding between PNA/DNA strands is stronger than between DNA/DNA strands due to the lack of electrostatic repulsion. Mixed base PNA molecules are true mimics of DNA molecules in terms of base-pair recognition. PNA/PNA binding is stronger than PNA/DNA binding.

The term "protein" is used herein interchangeably with the term "polypeptide" and refers to at least one polymer composed of natural or artificial amino acids.

The polymer comprised by a reporter molecule may also be selected from a polysaccharide, pullulan, schizophyllan, scleroglucan, xanthan, gellan, O-ethylamino guaran, chitin, chitosan, derivatized cellolosic, hydroxylated starch, carrageenan, alginate, agarose, synthetic polysaccharide, vinyl polymer, poly ethylene glycol (PEG) or polypropylene glycol or poly(ethylene oxide-co-propylene oxides) containing polymer backbones including linear, comb-shaped or branched dendrimer, poly amino acid, poly(ethylene imine), or pluriol.

In some embodiments the polymer may be a mixed polymer comprised of two or more different polymers described above.

In some preferred embodiments the polymer may comprise dextran. In another preferred embodiments the polymer may comprise at least one nucleic acid. In another preferred embodiments the polymer may comprise at least one nucleic acid analog. In another preferred embodiment the polymer may consist of or comprise L30 molecule. In other preferred embodiments the polymer may comprise at least one polypeptide.

As already mentioned, the polymer may be conjugated with a detectable label. In some embodiments, the detectable label may be conjugated to the polymer directly, i.e., covalently attached to the polymer, in other embodiments the detectable label may be conjugated to the polymer indirectly via a linker. Many such linkers are known in the art. Non-limited examples include polyethylene glycol and poly amides. A linker molecule in one embodiment may comprise 5-15 atoms, in another embodiment it may comprise 15-30 atoms, in another embodiment it may comprise more than 35 atoms, for example 36-45, in some embodiments the linker may comprise more than 45 atoms. One preferred embodiment of such linker molecule is L30 described above.

As mentioned above, L30 in some embodiments may serve as a backbone polymer of the reporter conjugate molecule. Some of such embodiments are described below in the provided examples (Examples 1.1-1.8) and shown in FIG. 2. In some other embodiments L30 may serve as linker grouping for the linking detectable labels to the polymer.

In some embodiments, 1-500 detectable label molecules may be directly or indirectly linked to a polymer molecule. In some embodiments, the detectable label is an enzyme and the number of enzyme molecules linked to each polymer molecule is 1-200, 2-50, 2-25. In some embodiments, the detectable label is a gold particle, a dye, a low molecular weight fluorochrome and the number of detectable substances linked to each polymer molecule is 1-500, 1-200, 1-100, 10-100, 20-50, 50-100, 1-50, 2-30, 10-20. In some embodiments, the detectable label is a protein fluorochrome, and the number of detectable molecules linked to a polymer molecule is 1-50, 2-20. In some other embodiments the detectable label is a nucleic acid or nucleic acid analog, e.g., an oligonucleotide or PNA molecule, and the number of detectable molecules linked to a polymer is 1-200, 2-50, 2-25.

Many methods of forming polymeric conjugates are known in the art and can be used to make the polymeric conjugates of the invention. In some embodiments a detectable substance, if desired, can be chemically linked, or conjugated, to a polymeric backbone. In some embodiments, the polymer conjugate is formed by covalent coupling amino groups to conjugated double bonds. The polymer may be activated with vinylsulfon and mixed with a detectable substance to form the polymer conjugate. In other embodiments, aldehydes are used to activate a polymeric backbone, e.g., dextrans which are then mixed with a detectable substance. Yet another method of preparing polymeric conjugates is by using so called chemo selective coupling schemes for coupling the components together, e.g., enzymes or other molecules can be derivatized with thiol reactive maleimide groups before being covalent coupled to an thiol modified polymeric carrier or backbone. Other embodiments described below permit the reagents themselves to form conjugates, e.g. the detectable substance.

As mentioned above, the polymer may serve on its own as a reporter molecule and not comprise any detectable label. Non-limited examples of such polymers may be nucleic acids, nucleic acid analogs and proteins.

Small Reporter Molecules

As already discussed above, the reporter may be a small molecule. By "small molecule is meant non-polymeric molecule of not more than 3000 Da, typically, from around 200 to around 1000 Da, for example around 500 Da. Typically such small reporter molecule is soluble in the media of the invention which comprises a cross-linker. The invention relates to any kind of such small molecule which can be deposited from the media in the presence of a peroxidase.

The small molecule may by a directly detectable substance. Examples of such substances include but not limited to 5-(and 6)-carboxyfluorescein, 5- or 6-carboxyfluorescein, 6-(fluorescein)-5-(and 6)-carboxamido hexanoic acid, fluorescein isothiocyanate, rhodamine, tetramethylrhodarnine, Cy2, Cy3, Cy5, AMCA, PerCP, R-phycoerythrin (RPE) allophycoerythrin (APC), Texas Red, Princeton Red, Green fluorescent protein (GFP) coated CdSe nanocrystallites, DNP, digoxiginin, luminol, isoluminol, acridinium esters, 1,2-dioxetanes and pyridopyridazines, and radioactive isotopes of hydrogen, carbon, sulfur, iodide, cobalt, selenium, tritium, and phosphor. The chromogenic substance may be selected form 3,3',5,5'-Tetramethylbenzidine (TMB), 10-acetyl-3,7-dihydroxyphenoxazine (ADHP), 3-amino-9-ethylcarbazole, 4-chloro-1-naphtol (AEC), ophenilenediamine (OPD), 2,2"-azido-bis(3)-ethylbenzthiazoline-6-sulphonic acid, 5-amino-243-[5-amino-1, 3-d ihydro-3, 3-dimethyl-1-(4sulfobutyl)-2H-indol-2-ylidene]-1-propenyl]-3,3dimethyl-1-(4sulfobutyl)-3H-Indolium. In one embodiment, the detectable small molecule may be a substrate for a peroxidase, preferably horse radish peroxidase (HRP). In one preferred embodiment the detectable small molecule is 5-amino-2-[3-[5-amino-1,3-3-dimethyl-1-(4sulfobutyl)-2H-indol-2-ylidene]-1-propenyl]-3,3dimethyl-1-25 (4sulfobutyl)-3H-Indolium.

In some embodiments the small molecule may be a molecule which cannot be detected directly, e.g. a substance which is not capable to become colored, fluorescent or chemiluminescent, e.g. biotin, or a substrate of a peroxidase enzyme such as ferulic acid or tyrosine. In such embodiments a detectable substance may be coupled to this kind of small molecule. For example the small molecule and detectable substance may be derivatized, e.g., with vinyl groups. Polymerization occurs by addition of a radical, which results in polymerization of the vinyl groups to form a polymeric conjugate. The conjugate thus will contain a poly vinyl backbone or blocks of poly vinyl. Active esters of acrylic acid can be used to activate the molecules. Generating free radicals can polymerize the derivatized molecules. Small molecule linkers with more than one vinyl group can be further added to help form a polymeric conjugate of a small molecule and a detectable substance. In some other embodiments, the small molecule and detectable substance can be derivatized with a cross binder. Examples of this method include the use of homobifunctional cross binders such as glutaric dialdehyde, hexan di isocyanate, dimethylapimidate, 1, 5-difluoro-2,4-dinitrobenzene, heterobifunctional cross binders like e.g. N-gamma-maleimidobytyroloxy succinimide ester, and zero length cross binders such as 1-ethyl-3-(3-dimethylaminopropyl)cabodiimide. By choosing the correct reaction conditions, the cross binders can form bridges between various functional groups in, e.g., the detectable substances and detectable agents to form a polymeric reporter molecule.

Peroxidase

Any enzyme which is capable of peroxidase activity is suitable for practicing the present invention.

According to the invention peroxidase activity is present in a target site. The term 'target site" refers to a site where the reporter molecule is to be deposited, e.g. a site comprising a biological or chemical marker. According to the invention the peroxidase activity is associated with at least one moiety of a peroxidase enzyme present in the target site. The term "one moiety" means that the peroxidase may be a natural or recombinant protein or a derivative thereof, e.g. a fragment thereof capable of peroxidase activity. in particular, the peroxidase may be selected from horse radish peroxidase (HRP) or soybean peroxidase (SP), fragments, recombinant or fusion proteins thereof. In one preferred embodiment the peroxidase is HRP.

In one embodiment the target site may be a site of any solid support which comprises peroxidase activity. Suitable supports include synthetic polymer supports, such as polystyrene, polypropylene, substituted polystyrene, e.g., aminated or carboxylated polystyrene; polyacrylamides; polyamides; polyvinylchloride; etc.; glass beads; agarose; nitrocellulose; nylon; polyvinylidenedifluoride; surface-modified nylon, etc. A peroxidase molecule can be directly or indirectly immobilized on these supports The target site may be a site of a biological sample, e.g. a site of a cell membrane, cell organelle, in case the biological sample comprises a cell, it may also be a site of a cell free biological sample, e.g. plasma sample or cell lysate or extract which is immobilized on a solid support such as described above. Such site will typically comprise a biological marker which may be a target molecule or structure. The peroxidase activity, will typically be associated with the target molecule indirectly, e.g. as part of a specific probe bound to the target molecule.

Media

The media of the invention is a media from which a soluble reporter molecule may be deposited in the presence of peroxidase activity. It is a water buffered solution with pH from about 4 to about 9, essentially comprising (i) a compound capable of cross-linking of at least two reporter molecules in the presence of peroxidase activity, wherein said compound is a molecule comprising at least two moieties of a peroxidase enzyme substrate, and wherein at least one of said two reporter molecules is a detectable molecule, and (ii) a peroxide compound.

Suitable soluble reporter molecules comprised in the media is in detail discussed above.

Suitable compounds capable of cross-linking of at least two reporter molecules in the presence of peroxidase activity is according to the invention are also in detail discussed above. In one preferred embodiment the cross-linking compound is DAB.

The amount of the cross-linking compound in the media may vary from about $10^{-5}$ to about $10^{-2}$M, such as from about $10^{-5}$ to about $10^{-3}$M, or from about $10^{-4}$ to about $10^{-2}$M, or from about $10^{-5}$ to about $10^{-4}$M, or from about $10^{-4}$ to about $10^{-3}$M, Concentration of the cross-linker may be optimized for different embodiments, e.g. when deposition of different reporters is concerned.

The media according to the invention comprises a peroxide compound. The peroxide compound may be selected from organic peroxides such as tent-butyl peroxide, ditert-butyl peroxide, peracetic acid, or it may be an adduct of hydrogen peroxide, such as hydrogen peroxide urea adduct. In some embodiments hydrogen peroxide ($H_2O_2$) may be preferred peroxide. The amount of the peroxide compound in the media is vary from about $10^{-4}$ to about $10^{-2}$M in different embodiments.

The media may further comprise an organic modifier and an organic modifier and organic or inorganic salt.

The inorganic salt may be selected form e.g. sodium chloride, magnesium chloride, potassium chloride, calcium chloride, sodium phosphate, or ammonium sulfate.

In other embodiments the media may comprise an organic salt, such as sodium acetate, ammonium acetate or imidazole salts, e.g. imidazole hydrochloride.

The concentration of salt in the media may range from approximately $10^{-3}$m to saturation, e.g. from approximately 20 mM to approximately 200 mM, or from approximately 50 mM to approximately 500 mM. In one preferred embodiment, the media may comprise salt in the amount from approximately 10 mM to 500 mM. In another preferred embodiment the medium may be free of salt.

Typically the pH value of the media may vary from around 4 to around 9. Any buffer with a suitable buffer capacity may be used, e.g. phosphate buffered saline (PBS), imidazole buffer. Other suitable buffers may be found in Good, N E., et al (1966) Hydrogen ion buffers for biological research. Biochem. 5(2), 467-477. The pH value of the media may be essential for depositing the reporter; it may be optimized depending on the nature of the reporter.

The media may in different embodiments further comprise:
(i) an organic modifier and/or
(ii) an enzyme enhancer, and/or
(iii) an iron chelator, and/or
(iv) a detergent, and/or
(v) an anti-microbial agent By the term "organic modifier" is meant any non water solvent which enhances the solubility of the reporter. In such embodiments it is sufficient that the modifier is present in the media in the amount of around 1% (v/v or w/v), however, in some embodiments higher concentrations of the organic modifier may be required. The organic modifier may for example be polyethylene glycol (PEG). Other examples include but not limited to organic modifiers selected from the group essentially consisting of lower alcohols, N-Methyl pyrolidone (NMP), dimethylsulphoxide (DMSO), mono- and diethylene glycol, sulpholane, N,N-dimethylformamide (DMF). In some embodiments it may be advantageous to use polyethylene glycol (PEG), e.g. PEG2000. The concentration of polyethylene glycol in the media in these cases may vary from about 0.1% (v/v) to about 20% (v/v), for example from about 1% (v/v) to about 15%, such as 5-10% (v/v).

By the term "enzyme enhancer" is meant any compound which enhances the catalytic activity of peroxidase. Such enzyme enhancer may be selected from the group essentially consisting of phenylboronic acid derivatives and divalent metal ions such as nickel or calcium. Concentration of the enzyme enhancer may vary from about $10^{-7}$ to about $0^{-3}$ M.

The iron chelator may be ethylene diamine tetra acetic acid (EDTA) or ethylene diamine hydroxyl phenylacetic acid type chelator (EDHPA). Concentration of the iron chelator may vary from about $10^{-6}$ to about $10^{-2}$ M.

The detergent may be selected from polyethylenglycol-p-isooctyphenyl ether (NP-40), a surfactant selected from the surfactants based on polyoxyethylene sorbitanmonolaurate (Tween), or a surfactant based on block copolymers (pluronic etc.). Concentration of the detergent may vary from about 0.001% to about 5%.

According to the invention the composition of the media is a stable solution. The term "stable" in the present context means that the capability of the media to serve as a reaction media for the peroxidase-mediated reporter deposition remains to be essentially unchanged during substantial periods of time; such as the media may tretain its reactive capability unaffected for at least 4 hours at room temperature.

The media can also be preserved for longer periods of time. To prolong the shelf-life of the media it may be recommended to store the media at temperatures below 20° C., e.g. at 410° C., and/or to add to the media an anti-microbial compound. The anti-microbial compound may be any anti-microbial compound commonly used for such purpose, e.g. sodium azid, Proclin™ or Bronidox®.

The media described above is a reaction media for depositing a reporter in a target site comprising peroxidase activity, e.g. a site comprising a biological marker.

2. Method of Detection of a Target in a Biological Sample

The method of deposition of a reporter in a target site described above may advantageously be used for detecting biological markers associated with this target site, e.g. biological molecules such as nucleic acids, proteins, etc. because the target site may be a site of a biological sample, e.g. a site of a cell membrane, cell organelle, in case the biological sample comprises a cell, or it may be a site of a cell free biological sample loaded on a solid support, e.g. plasma sample or cell lysate or cell extract which are immobilized on a solid support such as described above. The term "biological marker" means in the present context a molecule, molecular complex or structure that is specific for a biological species, cell type, cell compartment, physiological condition, etc. Non-limited examples of such biological marker include but not-limited to a particular genetic sequence, protein or another biological molecule, chromosomal or membrane structure, virus etc. which is associated with a particular disease. Biological markers are commonly used in medical diagnostic as markers of particular diseases and therapeutic targets.

Accordingly, a further aspect of the invention relates to a method of detection of a biological marker in vitro comprising the following steps:
a) incubating a biological sample presumably comprising a biological marker with one or more probes, wherein the least one of said one or more probes comprises at least one moiety of horse radish peroxidase (HRP), thereby forming a complex of the biological marker with the at least one probe comprising at least one moiety of HRP, and thereby forming a target site;
b) incubating the sample comprising the target site of (a) in a media comprising a reporter and a cross-linker, thereby depositing the reporter in the target site, i.e, in the site where the complex of the biological marker with the at least one probe comprising at least one moiety of HRP, is present;
c) detecting the deposited reporter of (b), and thereby detecting the biological marker.

Step (a)

Biological sample comprising a biological marker may be any biological sample comprising intact or damaged cells, e.g. a body tissue sample or cell lysate.

Non-limiting examples of the biological sample of the invention include:
a sample of liquid media comprising suspended cells, e.g. blood sample, clonal cells suspension or suspension of dissociated cells of a body tissue.
a sample of a body tissue, e.g. a biopsy sample; The tissue sample may be a fresh tissue sample, or it may be a sample of preserved tissue, e.g. formalin fixed and paraffin embedded tissue sample.
a sample of a tumor;
a sample derived from any living organism, e.g., animal, plant, bacteria etc. It may comprise eukaryotic cells or prokaryotic cells or both. It may be a cell smear.
a sample comprising viral particles, debris thereof, or viral products, e.g., viral ]0 nucleic acids, proteins, peptides, etc.

The biological sample presumably comprising a biological marker is according to the method of the invention incubated with at least one probe comprising at least one moiety of HRP or moiety of another peroxidase enzyme.

The term "incubating" means that the sample is maintained in a media comprising a probe (or a media comprising a cross-linker and a reporter (step (b)) during a certain period of time. This period of time may vary from 1-3 min to 1-2 hours or longer, e.g. overnight. Incubation may be performed at different temperatures depending on different embodiments, e.g. the type of biological marker molecule to be detected or type of probe and/or reporter used for the detection.

One probe or more probes which the sample being incubated specifically recognize and bind to a biological marker present in the sample.

The probes which recognize the biological marker are capable of specific binding to this marker and only to this marker. Typically such probes are members of specific binding pairs.

A number of different specific binding pairs are known in the art. In one embodiment the members of a specific binding pair may be two antibody molecules. In another embodiment, members of a specific binding pair may be two complementary nucleic acids. In another embodiment, the members of a specific binding pair may two nucleic acid analog molecules. In another embodiment the member of a specific binding pair may be a members of particular receptor-ligand binding pairs.

A probe which is capable of specifically binding to the biological marker and is the member of a specific binding pair, e.g. a primary antibody probe, is designated herein as a first probe. The first probe may be optionally labeled with a moiety of peroxidase enzyme.

In one embodiment the first probe may comprise at least one moiety of HRP or another peroxidase enzyme, e.g. soybean peroxidase (SP). A non-limiting example of such probe may be a HRP-labeled primary antibody molecule or a derivative thereof, or HRP-labeled nucleic acid probe. Such first probes specifically bind to the corresponding biological markers and label these biological markers with peroxidase activity and form thereby target sites.

In another embodiment the first probe may be not labeled, i.e. not comprise a moiety of a peroxidase. In this embodiment, a moiety of peroxidase may be linked to a target site through a second probe. The second probe is a probe which is capable of specific binding to the first probe, e.g. is the other member of a specific binding pair. Non-limiting examples of such probes may be secondary antibodies molecules of derivatives thereof, nucleic acid probes or members of receptor-ligand binding pairs. Such second probe may comprise at least one moiety of HRP or another peroxidase enzyme e.g. soybean peroxidase (SP). By binding to the first probe the second probe comprising peroxidase activity will label the site where the biological marker is found with this peroxidase activity and form thereby a target site.

In another embodiment, both the first and second probe may comprise at least one moiety of peroxidase enzyme, e.g. HRP and/or SP.

The step (a) may in some embodiments include several sub-steps where third and fourth probes are used. For example, before proceeding to step (b) of the procedure, the sample comprising a biological marker may be sequentially incubated with multiple probes, whereof first probes are capable of binding to the biological marker, whereas second, third and the other probes are capable of binding to each other, i.e. second probes to first probes, third probes to second probes, etc., and thus one marker molecule will be associated with many different probes. Every probe may comprise one or more moieties of a peroxidase enzyme. Such multi-probe labeling of a single biological marker may be used when a high accumulation of peroxidase activity in a single target site is desirable. This may be useful for enhancement of reporter deposition in a single target site.

Before proceeding to step (b) of the method, step (a) may be repeated as many times as desirable in order to increase accumulation of peroxidase activity in the target site.

Step (b):

The sample comprising a target site formed on step (a) is further incubated in a media comprising a cross-linker and a reporter according to the invention.

Details of the composition of the media suitable for the incubation of step (b) are discussed above. The composition of the media may vary depending on the species of reporter and cross-linker molecules used and nature of a particular biological marker to be detected. For example, the media may comprise DAB as a cross-linker when the reporter is a reporter comprising a polymer backbone to which several fluorescent labels are attached (e.g. reporter molecules described in Example 6 or 7).

Incubation of step (b) according to the invention results in that the reporter molecules present in the incubation media are deposited in the target sites, i.e. the sites of a biological sample which comprise a biological marker labeled with peroxidase activity. Because of the reporter is deposited only in or around the site of the presence of peroxidase activity, the site of its deposition is the site where the biological marker is present.

In one embodiment, step (b) may comprise at least two incubations: incubation of the sample in the media comprising a cross-linker (i.e. without a reporter); following by (ii) incubation of the sample in the media comprising both cross-linker and reporter.

Step (b) may optionally be repeated.

Step (c):

As discussed above, the reporter molecule is a detectable molecule. Different embodiments of detectable reporter molecules are described above.

Detection of the reporter may be "direct"—the one-step detection in case the deposited reporter may give off a chromogenic, radioactive or fluorescent signal which can be detected by a suitable means.

Detection may be "indirect"—comprise several steps of detection, e.g. when the deposited reporter is a non-labeled member of a specific binding pair, e.g. antibody or nucleic acid probe. Such reporter may be detected by a procedure comprising several steps of detection on which steps a number of different detectable probes may be used. Every probe used on any step may comprise multiple detectable labels. The labels may also be enzyme labels, e.g. moieties HRP. Such indirect detection of the deposited reporter in some embodiments may be preferred, e.g. when a signal associated with the deposited reporter in a target site is desirable to amplify.

A sample comprising the deposited reporter to which a reporter recognizing probe is bound may be incubated further in the media comprising a cross-linker and another reporter. In case the reporter bound probe comprises a moiety of a peroxidase, this further incubation may be used for deposition of another reporter in the same target site; this may be used for amplification of the initial signal emanating from the target site and thus for enhancement of sensitivity of the detection, or it may be used for labeling the target site with a detectable label which is different from the label used in the initial deposition. Such further incubation may be repeated several times.

The method of detection of biological targets described above may be used in a variety of assay formats. Some embodiments of these assay formats are described below and illustrated by non-limiting working examples of the invention.

Assay Formats

Target molecules comprised by cells of a cell suspension may be detected employing the method described above in any suitable assay format, for example in flow cytometry (FC), or ELISA, or immunohytochemistry (IHC), or in situ hybridization (131-1).

In one embodiment the biolodical sample may be a suspension of cells, Target molecules or structures of cells in suspension may be detected using FC, ELISA, IHC or ISH. When ELISA, IHC or ISH are used for the detection cells of the suspension are to be attached to a solid support, e.g. ELISA plate or ICH slide.

In another embodiment the biological sample may be a slice of a body tissue. Target molecules or structures of cells of such samples will be typically detected using IHC or ISH.

IHC and ISH assay formats usually require a series of treatment steps conducted on a tissue section mounted on a suitable solid support for microscopic inspection, or the production of photomicrographs, e.g., a glass slide or other planar support, to highlight by selective staining certain morphological indicators of disease states or detection of biological markers. Thus, for example in IHC, a sample is taken from an individual, fixed and exposed to antibodies which specifically bind to the biological marker of interest. The sample processing steps may include, for example, antigen retrieval, exposure to a primary antibody, washing, exposure to a secondary antibody (optionally coupled to a HRP moiety), washing, and exposure to a tertiary antibody linked to one or more HRP moieties. Washing steps may be performed with any suitable buffer or solvent, e.g., phosphate-buffered saline (PBS), tris buffered saline (TBS), distilled water. The wash buffer may optionally contain a detergent, e.g., Tween 20.

As mentioned above, there are in general two categories of histological samples: (1) preparations comprising fresh tissues and/or cells, which generally are not fixed with aldehyde-based fixatives, and (2) fixed and embedded tissue specimens, often archived material.

Before performing detection of a target in the IHC assay format, a pre-detection procedure is to be performed. It may involve the steps of: cutting and trimming tissue, fixation, dehydration, paraffin infiltration, cutting in thin sections, mounting onto glass slides, baking, deparaffination, rehydration, antigen retrieval, blocking steps, applying primary antibody, washing, applying secondary antibody enzyme conjugate and washing, In ISH, a sample is taken from an individual, fixed and exposed to a nucleic acid probe which hybridizes by virtue of complementary base pairing to the nucleic acid of interest. The biological sample typically comprises a detectable nucleic acid, such as DNA and RNA, including messenger RNA. Detection of DNA/RNA levels may indicate the level of expression of a particular gene, and hence may be used to detect a condition (such as a disease condition) of a cell, tissue, organ or organism. The nucleic acid in the sample is typically denatured to expose binding sites. The probe is typically a double or single stranded nucleic acid, such as a DNA or RNA, or a nucleic acid analog, such as PNA. The amount of the relevant target protein or nucleic acid detected by such techniques is then assessed to determine whether it is above a certain pre-determined minimum threshold or compared to a known standard, and therefore, diagnostically relevant. Suitable treatment may then be planned for the individual if necessary.

Many methods of fixing and embedding tissue specimens are known, for example, alcohol fixation and formalin-fixation and subsequent paraffin embedding (FFPE).

Fixatives are needed to preserve cells and tissues in a reproducible and life-like manner. To achieve this, tissue blocks, sections, or smears are immersed in a fixative fluid, or in the case of smears, are dried. Fixatives stabilize cells and tissues thereby protecting them from the rigors of processing and staining techniques.

Any suitable fixing agent may be used, for example, ethanol, acetic acid, picric acid, 2-propanol, 3,3'-diaminobenzidine tetrahydrochloride dihydrate, acetoin (mixture of monomer) and dimer, acrolein, crotonaldehyde (cis+trans), formaldehyde, glutaraldehyde, glyoxal, potassium dichromate, potassium permanganate, osmium tetroxide, paraformaldehyde, mercuric chloride, tolylene-2,4-diisocyanate, trichloroacetic acid, tungstic acid. Other examples include formalin (aqueous formaldehyde) and neutral buffered formalin (NBF), glutaraldehyde, acrolein, carbodiimide, imidates, benzoequinone, osmic acid and osmium tetraoxide.

Fresh biopsy specimens, cytological preparations (including touch preparations and blood smears), frozen sections and tissues for immunohistochemical analysis are commonly fixed in organic solvents, including ethanol, acetic acid, methanol and/or acetone.

To facilitate the specific recognition in fixed tissue, it is often necessary to retrieve or unmask the targets, i.e., the biological markers of interest, through pre-treatment of the specimens to increase reactivity of the majority of targets. This procedure is referred to as "antigen retrieval", "target retrieval" or "epitope retrieval", "target unmasking" or "antigen reagents unmasking." An extensive review of antigen retrieval (antigen unmasking) may be found in Shi et al. 1997, *J Histochern Cytochem,* 45(3):327.

Antigen retrieval includes a variety of methods by which the availability of the target for interaction with a specific detection reagent is maximized. The most common techniques are enzymatic digestion with a proteolytic enzyme (for example proteinase, pronase, pepsin, pepsin, trypsin or neuraminidase) in an appropriate buffer or heat induced epitope retrieval (HIER) using microwave irradiation, heating in a water bath, a steamer, a regular oven, an autoclave or a pressure cooker in an appropriately pH stabilized buffer, usually containing EDTA, EGTA, Tris-HCl, citrate, urea, glycin-HCl or boric acid. Detergents may be added to the HIER buffer to increase the epitope retrieval or added to the dilution media and/or rinsing buffers to lower non-specific binding.

The antigen retrieval buffer is most often aqueous, but may also contain other solvents, including solvents with a boiling point above that of water. This allows for treatment of the tissue at more than 100° C. at normal pressure.

Additionally, the signal-to-noise ratio may be increased by different physical methods, including application of vacuum and ultrasound, or freezing and thawing of the sections before or during incubation of the reagents.

Endogenous biotin binding sites or endogenous enzyme activity (for example phosphatase, catalase or peroxidase) may be removed as a step in the detection procedure, e.g., endogenous biotin and peroxidase activity may be removed by treatment with peroxides. Endogenous phosphatase activity may be removed by treatment with levamisole. Endogenous phosphatases and esterases may be destroyed by heating.

Blocking of non-specific binding sites with inert proteins like, horse serum albumin (HSA), casein, bovine serum albumin (BSA), and ovaibumin, fetal calf serum or other sera, or detergents like Tween20, Triton X-100, Saponin, Brij or Pluronics may be used. Blocking non-specific binding sites in the tissue or cells with unlabeled and target non-specific versions of the specific reagents may also be used.

Samples may also be prepared and target molecules detected using the free floating technique. In this method a tissue section is brought into contact with different reagents and wash buffers in suspension or freely floating in appropriate containers, for example micro centrifuge tubes.

The tissue sections may be transferred from tube to tube with different reagents and buffers during the staining procedure using for example a "fishing hook like" device, a spatula or a glass ring. The different reagents and buffer can also be changed by gentle decantation or vacuum suction. Alternatively, containers with the tissue sections can be emptied into a special staining net, like the Corning "Netwells" (Corning,) and the tissue section washed before being transferred back into the tube for the next staining step.

All the steps, including for example fixation, antigen retrieval, washing, incubation with blocking reagents, immuno-specific reagents and the peroxidase-mediated reporter deposition, are done while the tissue section is floating freely or withheld on nets. After deposition of the reporter, the tissue section is mounted on slides, the reporter is detected and slide covered with a cover slip before being analyzed, e.g., by light or fluorescent microscopy.

In some embodiments, the tissue section may be mounted on slides following the critical incubation with the immuno-specific reagents following the procedure (a) of the method.

The rest of the process of detection is then conducted on the slide mounted tissue sections.

Detectable Biological Markers

Detectable by the method, the biological marker may be any molecule or structure present in a sample, preferably in a biological sample, e.g. a protein, glycoprotein, lipoprotein, phosphoprotein, methylated protein, or a protein fragment, e.g., a peptide or a nucleic acid, e.g., DNA, RNA, it a lipid, a glycolipid, or a sugar, a polysaccharide, or a starch. The biological marker may be expressed on the surface of the biological sample, e.g., membrane bound. The marker may be contained in the interior of the biological sample, i.e., within the cell membrane, e.g., within the cytoplasm, within the nucleus, within an intracellular compartment or organelle. The biological marker may be a cellular structure, such as a membrane microdomain, ion channel, chromosomal structure, etc., or it may be a molecular complex, e.g. RNA-protein complex, etc. A biological marker is preferably a specific biological marker, for example it is a marker of a normal or pathological condition, or it is specific for a particular cell or tissue, or specific for a particular biological species.

Detection of such biological marker may be useful in diagnosis and treatment of pathological conditions.

The invention relates to detection at least one biological marker in a biological sample. Accordingly the invention also provides for detecting multiple biological markers. e.g., two, three, in a given sample and thus provides a method of obtaining data, e.g., diagnostic information, concerning expression of biological markers, panels of proteins, genes or combinations of one or more proteins and one or more genes. As an example, but not as a limitation, HER2 protein and the HER2 gene can be screened simultaneously in a cancer diagnostic assay, e.g., an assay for breast cancer. Another non-limiting example may include screening for three markers, e.g., to detect cervical cancer. The markers may include Ki67/mib-1, as well as the cellular proliferation marker, p16(INK4a), along with a marker, e.g., a protein or nucleic acid, for human papilloma virus. Yet another non-limiting example includes screening for multiple markers associated with prostate cancer. These markers may include AMACR P504S, high molecular weight cytokeratin (HMW-CK), and p63. Screening this combination of markers provides a method to distinguish benign prostate tumors from malignant ones.

It is desirable to minimize cross-reactivity between binding agents, e.g. where multiple markers are detected. This can be accomplished by using different probes and different reporter molecules in the detection procedures. An example of such a system is depicted in FIG. 3 where two different biological markers, e.g. two different cellular receptors, are detected using the following steps:

(1). incubating the sample with first probe 1 (1P1) (e.g. an HRP-conjugated antibody AB1)

(2). incubating the sample (1) with reporter 1 (R1) (e.g. ferulic acid-PNA1 conjugate) in the presence of a cross-linker (e.g. DAB)

(3). incubating the sample (2) with hydrogen peroxide (>3% v/v)

(4). incubating the sample (3) with first probe 2 (1P2) (e.g. HRP-conjugated antibody AB2)

(5). incubating the sample (4) with reporter 2 (R2) (e.g. ferulic acid-PNA2 conjugate (6) incubating the sample (5) with second probe 1 (2P1) (e.g. PNA1'-FITC) and with second probe 2 (2P2) (e.g. PNA2'-Texas Red)

As the result, the green fluorescent signal (emanating from PNA1'-FITC) is detected from the target site where R1 is deposited, the red fluorescent signal (emanating from PNA2'-Texas Red) is detected from the target site of R2 deposition, and the yellow signal where both R1 and R2 are deposited, i.e. from the site were both targets A1 and A2 are present.

All steps of the method (from (a) to (c)) may be completed within 2-20 min. Such rapid detection may be advantageously used for automated or semi-automated detection of target biological markers. Automated staining devices are known in the field and the method may be adapted for these devices.

Automated staining devices may be used in various embodiments of the invention, for example for the detection of multiple biological markers. Detection of multiple markers frequently requires balancing of the signals emanating from the different detectable substances. Automated procedure may include multiple steps of amplification of the signals emanating from target biological markers. It is especially advantageous when multiple markers are to be detected.

Antibody Probes

The term "probe" designates a substance that can specifically binds to a target, wherein the target may be a biological marker, another probe, reporter, or any molecule associated with said biological marker, another probe or reporter.

In one embodiment the probe is an antibody probe.

Antibody, as used herein, means an immunoglobulin or a part thereof, and encompasses any polypeptide comprising an antigen-binding site regardless of the source, method of production, and other characteristics. The term includes for example, polyclonal, monoclonal, monospecific, polyspecific, humanized, single-chain, chimeric, synthetic, recombinant, hybrid, mutated, and CDR-grafted antibodies. A part of an antibody can include any fragment which can still bind antigen, for example, an Fab, F(ab')$_2$, Fv, scFv. The origin of the antibody is defined by the genomic sequence irrespective of the method of production.

Primary antibody, as used herein, refers to an antibody that specifically binds to a biological marker of interest present within the biological sample. In certain embodiments the primary antibody may be polymerized. Primary antibodies may be derived from any warm blooded species, e.g. mammals, birds.

Secondary antibody, as used herein, refers to an antibody that has an antigen binding domain that specifically binds to a first probe, e.g., a primary antibody, or a hapten deposited in the target site, or hapten linked directly or indirectly to a first probe.

Tertiary antibody, as used herein, refers to an antibody that has an antigen binding domain that specifically binds to a second probe (e.g., a secondary antibody) or a hapten linked to a second probe or a hapten linked to polymer conjugated to a second probe, or hapten deposited in the target site.

Sometimes an antibody may function both as a secondary and a tertiary antibody.

Antibodies used in the invention, including primary antibodies, secondary antibodies and tertiary antibodies, may be derived from any mammal species, e.g., a rat, a mouse, a goat, a guinea pig, a donkey, a rabbit, horse, lama, camel, or any avian species e.g., chicken, duck. Derived from any mammal or avian species, as used herein, means that at least a part of the nucleic acid sequence encoding a particular antibody originated from the genomic sequence of a specific mammal, e.g., a rat, a mouse, a goat, or a rabbit or a specific bird e.g., chicken, duck. The antibody may be of any isotype, e.g., IgG, IgM, IgA, IgD, IgE or any subclass, e.g., IgG1, IgG2, IgG3, IgG4.

In certain embodiments the primary antibody contains an antigen binding region which can specifically bind to a biological marker expressed by cells comprising a biological sample. The marker may be expressed on the cell surface or within the cell membrane, i.e., on the interior of the cell, e.g., within the cytoplasm, within the nucleus, within the endoplasmic reticulum. In some embodiments the biological marker is secreted from the cell and thus is present in solution, e.g., in cell culture media, in blood or plasma.

In certain embodiments, the secondary antibody contains an antigen binding region which specifically binds to the primary antibody, e.g., the constant region of the primary antibody.

In certain embodiments, the secondary antibody is conjugated to a polymer. In some embodiments, the polymer is conjugated with 2-20 secondary antibodies. In other embodiments, the polymer is conjugated with 2-10 secondary antibodies.

In certain embodiments, the tertiary antibody contains an antigen binding region which specifically binds to the secondary antibody, e.g., a constant region of the secondary antibody, or a hapten linked to the secondary antibody or a polymer conjugated to the secondary antibody. In certain embodiments, the tertiary antibody is conjugated to a polymer. In some embodiments, the polymer is conjugated with 1-20 tertiary antibodies. In other embodiments, the polymer is conjugated with 1-5 tertiary antibodies.

The antibodies that may be used in the methods and compositions of the invention include monoclonal and polyclonal antibodies, engineered antibodies including chimeric, CDR-grafted and artificially selected antibodies produced using phage display or alternative techniques.

Various techniques for producing antibodies have been described, see, e.g., Kohler and Milstein, (1975) *Nature* 256:495; Harlow and Lane, *Antibodies: a Laboratory Manual*, (1988) (Cold Spring Harbor Press, Cold Spring Harbor, N.Y.) incorporated herein by reference. Techniques for the preparation of recombinant antibody molecules is described in the above references and also in, for example, EP 0623679; EP 0368684; and EP 0436597.

Antibodies may be produced recombinantly or synthetically. Nucleic acids encoding antibodies may be isolated from a cDNA library. Nucleic acids encoding antibodies may be isolated from a phage library (see e.g. McCafferty et al. 1990, *Nature* 348:552, Kang et al. 1991, *Proc. Natl. Acad. Sci. USA* 88:4363; EP 0 589 877 B1). Nucleic acids encoding antibodies can be obtained by gene shuffling of known sequences (Mark et al. 1992, *Bio/Technol.* 10:779). Nucleic acids encoding antibodies can be isolated by in vivo recombination (Waterhouse et al. 1993, Mid. *Acid Res.* 21:2265). The antibodies used in the methods and compositions of the invention include humanized immunoglobulins (U.S. Pat. No. 5,585,089, Jones et al. 1986, *Nature* 332:323).

The antibodies may be altered antibodies comprising an effector protein such as a toxin or a label, e.g., a detectable substance.

Antibodies may be obtained from animal serum, or, in the case of monoclonal antibodies or fragments thereof, produced in cell culture. Recombinant DNA technology may be used to produce the antibodies according to established procedure, in bacterial, yeast, insect or mammalian cell culture. In certain embodiments, the selected cell culture system preferably secretes the antibody product.

Nucleic Acid Probes

In another embodiment a first probe may be or comprise a nucleic acid or nucleic acid analog molecule, e.g., a DNA molecule, an RNA molecule, a PNA molecule, for use in in situ hybridization. Nucleic acid probes may be synthesized chemically or produced recombinantly in cells (see e.g. Sambrook et al. (1989) *Molecular Cloning: A Laboratory Manual*, 2nd ed. Cold Spring Harbor Press). In some embodiments, the probe is comprised of a peptide nucleic acid (PNA). A peptide nucleic acid is a nucleic acid molecule in which the deoxyribose or ribose sugar backbone, usually present in DNA and RNA is replaced with a peptide backbone. Methods of making PNAs are known in the art (see e.g. Nielson, 2001, *Current Opinion in Biotechnology* 12:16) (hereby incorporated by reference). In other embodiments, the probe is comprised of locked nucleic acids (LNA) (Sorenson et al. 2003, *Chem. Commun.* 7(17):2130). In some embodiments, the nucleic acid probe specifically binds to the biological marker, e.g., a nucleic acid molecule contained within the biological sample.

The nucleic acid probe, in particular embodiments, comprises at least a sequence that specifically hybridizes to a target sequence in the biological sample, e.g. a nucleic acid sequence such as a genomic DNA sequence or an mRNA sequence, under specific conditions of stringency. As used herein, the term "hybridization under stringent conditions," is intended to describe conditions for hybridization and washes under which nucleotide sequences that are significantly complementary to each other remain bound to each other. The conditions are such that sequences at least 70%, at least 80%, at least 85-90% complementary remain bound to each other. The percent complementary is determined as described in Altschul et al. (1997) *Nucleic Acids Res.* 25:3389-3402 (hereby incorporated by reference).

Specified conditions of stringency are known in the art and can be found in *Current Protocols in Molecular Biology*, John Wiley & Sons, Inc. (Ausubel et al. 1995 eds.), sections 2, 4, and 6 (hereby incorporated by reference). Additionally, specified stringent conditions are described in Sambrook et al. (1989) *Molecular Cloning: A Laboratory Manual*, 2nd ed. Cold Spring Harbor Press, chapters 7, 9, and 11 (hereby incorporated by reference). In some embodiments, the hybridization conditions are high stringency conditions, An example of high stringency hybridization conditions is hybridization in 4× sodium chloride/sodium citrate (SSC) at 65-70° C. or hybridization in 4×SSC plus 50% formamide at 42-50° C., followed by one or more washes in 1×SSC, at 65-70° C. It will be understood that additional reagents may be added to hybridization and/or wash buffers, e.g., blocking agents (BSA or salmon sperm DNA), detergents (SDS), chelating agents (EDTA), Ficoll, PVP, etc.

In some embodiments, the nucleic acid probes hybridize to a target sequence in a sample under moderately stringent conditions. Moderate stringency, as used herein, include conditions that can be readily determined by those having ordinary skill in the art based on for example, the length of the DNA. Exemplified conditions are set forth by Sambrook et al. *Molecular Cloning: A Laboratory Manual,* 2d ed. Vol. 1, pp. 1.101-104, Cold Spring Harbor Laboratory Press (1989) (hereby incorporated by reference), and include use of a prewashing solution of 5×SSC, 0.5% SDS, 1.0 mM EDTA (pH 8.0), hybridization conditions of 50% formamide, 6×SSC at 42° C. (or other similar hybridization solution, such as Stark's solution, in 50% formamide at 42° C.), and washing conditions of 60° C., 0.5×SSC, 0.1% SDS.

In some embodiments, the nucleic acid probes hybridize to a target sequence in a sample under low stringent conditions. Low stringency conditions may include, as used herein, conditions that can be readily determined by those having ordinary skill in the art based on, for example, the length of the DNA. Low stringency may include, for example, pretreating the DNA for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 ug/ml denatured salmon sperm DNA. Hybridizations are carried out in the same solution with the following modifications: 0.02% PVP, 0.02% Ficoll, 0.2% BSA, 100 pg/ml salmon sperm DNA, 10% (wt/vol) dextran sulfate, and 5-20×10$^6$ CPM probe is used. Samples are incubated in hybridization mixture for 18-20 hours at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C.

Other embodiments of the probes include peptide sequences, e.g. peptide sequences derived from protein or nucleic acid binding domains of different proteins, ligands of different cellular and nuclear receptors and their derivatives, small molecules which can bind specifically to certain structural units of large biological molecules, however, this is just a list of non-limiting examples of substances that can be used as probes for the purposes of the present invention.

EXAMPLES

1. Examples of Reporter and Cross-Linker Molecules of the Invention

ABBREVIATIONS

MBHA 4-Methylbenzhydrylamine
NMP N-Methyl Pyrolidon
HATU 2-(1 h-7-azabenzotriazole-1-yl)-1,1,3,3 tetramethyl uronium hexafluorophosphate; rnethenamminium
DIPEA Di/sopropyl EthylAmine
DCM Dichloro Methane
TFA TriFluoroacetic Acid
TFMSA TriFluor Methyl Sulphonic Acid
Fer Ferrulic acid
FLU Fluorescein
Tyr Tyrosine
Lys Lysine
Dex Dextran
HPLC High Performance Liquid Chromatography
equi. equivalent 1.1. Fer-L30-Lys(Flu)-NH$_2$ (D17158)

MBHA resin was downloaded with Fmoc-Lys(ivDDE) to a loading of 150 micro mol/g. 200 mg resin was de-Fmoc'ed with 20% piperidine in NMP, the subjected to one coupling with Boc-L30-OH (1.5 mL 0.26 M in NMP, preactivated with 0.9 equi. HATU, 2 equivalents DIPEA for 2 min) for 20 min. The ivDDE group was removed with 5% hydrazine in NMP, and the lysine side chain was labeled with carboxy fluorescein (Flu) (1.5 mL 0.2 M in NMP, preactivated for 2 min with 0.9 equi. HATU, 2 equi DIPEA) for 2×20 min. The resin was treated with 20% piperidine in NMP, NMP, DCM then DCM. The intermediate product H-L30-Lys(Flu)-NH$_2$ was cleaved of the resin with TFA:TFMSA:mCresol (7:2:1, 1.5 ml for 1 h), precipitated with diethyl ether, re-suspended in TFA, precipitated with diethyl ether, re-suspended in NMP and again precipitated with diethyl ether. It was made basic with 100 microL DIPEA and dissolved directly in 0.5 mL 0.3M Ferulic acid preactivated with 0.9 equi. HATU and 2 equi. DIPEA. After 25 min the crude product was precipitated with diethyl ether, dissolved in 450 microL NMP and 50 microL ethylenediamine. After 5 min the product was precipitated with diethyl ether, dissolved in 15% acetonitril in water (8 mL) and acidified with 100 microL TFA and subjected to RP-HPLC purification.

1.2. Fer-L150-Lys(Flu)-NH$_2$ (D17157)

MBHA resin was downloaded with Boc-Lys(Fmoc) to a loading of 100 micro mol/g. 100 mg resin was subjected to 5 coupling cycles with Boc-L30-OH (a. Coupling with Boc-L30-OH as in 1. b. Capping with 2% acetic anhydride in NMP: Pyridine 1:1, 2 min. c. De-Bc with 5% mCresole in TFA 2×5 Min.). The lysine side chain was De-Fmoc'ed and labeled with carboxy fluoresceine, as in 1. The intermediate product H-L150-Lys(Flu)-NH$_2$ was cleaved of the resin, and labeled N-terminally with Ferulic Acid and purified as in 1.1.

1.3. betaala-L90-Lys(Flu)-L90Lys(Flu)-L90-Lys(Flu)-NH2 (D16127)

Boc-L90-Lys(Fmoc)-L90-Lys(Frnoc)-L90Lys(Fmoc) was prepared on 0.5 g MBHA resin with standard solid phase chemistry (as in 1.1. and 1.2). Fmoc groups were removed from lysine side chains with 20% piperidine in NMP and the compound was subjected to repeated carboxy fluorescein labeling (3×30 min). Following removal Boc groups with TFA, the N-terminal was labeled on solid phase with betaalanine-N,N-di acetic acid (betaala) tert-butyl ester. Following cleavage from resin and HPLC purification, betaala-L90-Lys(Flu)-L90Lys(Flu)-L90-Lys(Flu)-NH2 was isolated.

1.4. H-Cys-L90-Lys(Flu)-L90Lys(Flu)-L90-Lys(Flu)-NH2 (D16126)

Boc-L90-Lys(Fmoc)-L90-Lys(Fmoc)-L90Lys(Fmoc) resin was prepared and labeled with fluorescein using the procedure described in 1.3. Following removal Boc groups the N-terminal was labeled with N-Boc-S(4-Methoxybenzyl)-Cys-OH. The compound was cleaved from the column and purified by HPLC:

tation, and labeled with Ferulic acid as in 1.1. The final product was isolated by HPLC.

Examples 1.5.-1.8. are the examples of cross-linker molecules of the formula (R1)n-(X)q-R2(m), wherein
R1 and R2 are different moieties of HRP substrate(s) (e.g. Fer or Tyr)
X is a linker molecule of the following formula

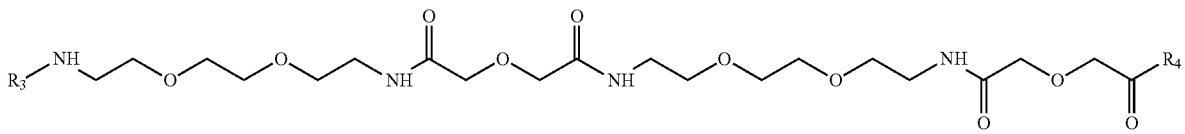

Molecules 1.1, 1.2, 1.3. and 1.4. are non-limited embodiments of reporters comprising Fluorescein residues.

1.5. Fer-Lys(Fer)-L30-Lys(Fer)-L30-Lys(Fer)-L30-Lys(Fer)-L30-Lys(Fer)-L30Lys(NH2)-NH2 (D17120)

To MBHA resin was sequentially coupled Boc-Lys(Fmoc) (2 cycles), Boc-L30-OH (5 cycles) and Boc-Lys(2ClZ)-0H. The intermediate product was cleaved from the resin in the presence of 10% thioanisol scavenger to remove 2ClZ-groups. The N-terminal and the 5 de-protected lysine side chains were labeled with Ferulic acid as in 1.1 (2×30 Min). The Fmoc group on the N of the C-terminal Lysine residues was then removed with 10% ethylene diamine in NMP prior to purification.

1.6. Fer-(Lys(Fer)-L30)$_5$-Lys(NH-betala((L90-Lys(Flu))3-NH$_2$)-NH$_2$(D17134)

betaala-L90-Lys(Flu)-L90Lys(Flu)-L90-Lys(Flu)-NH2 (compound 1.4) 500 nmol was dissolved in 88 microL NMP and 2 microL pyridine, and converted to cyclic anhydride by reaction with 10 microL diisopropyl carbodiimiide for 10 min. The anhydride was precipitated with diethyl ether, and the pellet was dissolved in 100 microL NMP comprising 250 nmol Fer-(Fer-L30)$_5$-Lys(NH$_2$)—NH$_2$. After 20 min 5 microL ethylene diamine was added, and after 5 min the product was precipitated with diethyl ether, acidified and HPLC purified.

1.7. Ac-(Tyr(OH)-L30)$_5$-L90-Lys(Flu)-L90-Lys(Flu)-Lys(Flu)-NH$_2$ (D18044)

Ac-(Tyr(2BrZ)-L30)$_6$-L90-Lys(Fmoc)-L90-Lys(Fmoc)-Lys(Fmoc) was prepared on MBHA resin. On solid phase the Fmoc groups were removed, and the lysine side chains labeled with carboxy fluorescein. Following cleavage from the resin, the product was HPLC purified.

1.8. Fer-Lys(Fer)-L60-Lys(Fer)-Lys(Fer)-L60-Lys(Fer)-Lys(Fer)-L30-Lys(NH$_2$)—NH$_2$ (D17140)

Boc-Lys(2ClZ)-L60-Lys(2ClZ)-Lys(2ClZ)-L60-Lys(2ClZ)-Lys(2ClZ)-L30-Lys(Fmoc) was prepared on MBHA resin. Following cleavage from the resin, the intermediate product H-Lys(NH$_2$)-L60-Lys(NH2)-Lys(NH2)-L60-Lys(NH$_2$)-Lys(NH$_2$)-L30-Lys(Fmoc) was isolated by precipiwherein R3 and R4 are residues of Lys,
and m, n and q are from 1 to 6.

Linear polymer cross-inkers (for example molecules 1.6. and 1.7, described above) bearing several residues of fluorescein, Ferulic acid (1.6) and/or tyrosine (1.7) are also embodiments of reporters that can be deposited by HRP in the presence of another cross-linker, e.g. DAB. Such linear relatively low molecular weight (MW<15 kDa) cross-linkers/reporters may be particular useful when the HRP enzyme moieties are bound to target sites which are not easily accessible or exposed, e.g. in cell nuclei such as DNA. Larger reporter molecules, for examples reporters comprising dextran molecules conjugated with tens and hundreds of labels (e.g. Flu and/or Fer and/or Tyr), such as for example molecule 1.9. (described below), may be used when peroxidase enzyme moieties are located in more easy accessible target sites.

1.9. Dex70 Conjugated with Cross-Linker 1.5. and Cross-Linker 1.4. (D17130)

Dextran MW 70 kDa, activated with divinyl sulphone, 10 nmol, was reacted with Fer-(Fer-L30)$_5$-Lys(NH$_2$)—NH$_2$ (compound 1.5) 500 nmol, in a total volume of 300 microL 0.16M NaHCO$_3$ pH 9.5 for 30 min at 40 C. After a slight precipitation was observed, further 100 microL water was added and the reaction was allowed to proceed for another 30 min. Further 200 microL 0.15 M NaHCO$_3$ was added together with 500 nmol H-Cys-L90-Lys(Flu)-L90Lys(Flu)-L90-Lys(Flu)-NH2 (compound 1.4). After 1 h at 40 C, the reaction mixture was quenched by addition of 50 microL 0.165M cystein for 30 min, solution was filtered, and the product was purified by FPLC on superdex 200 with 20% EtOH in aqueous solution containing 10 mM CHES, pH 9.0, and 0.1 M NaCl. The product eluted was a Dextran conjugate comprising around 56 Fluorescein and 113 Ferulic Acid residues.

1.10. Goat-anti-Mouse-Dex70-HRP (D18033)

13.7 nmol divinylsulphone were activated 70 kDA MW dextran and reacted with 602 nmol 5 HRP were in 600 microL buffer (100 mM NaCl, 25 mM NaHCO$_3$, pH 9.5) for 3 h at 30 C. Then 41.1 nmol Goat-anti-Mouse F(ab)$_2$ antibody in 105 microL water was added, and the reaction was continued for additional 16 h. The reaction mixture was quenched by addition of 70 microL 0.165M cystein for 30 min and the product was purified on superdex 200 in 100 mM NaCl, 10 mM HEPES pH 7.2. The eluded product was a Dextran conjugate comprising Goat-anti-Mouse (GaM) and HRP (Ratio dex:GaM:HRP=1:1:1).

1.11. Anti-FITC-Dex70-HRP (D18058)

10 nmol divinylsulphone activated 70 kDA MW dextran and 440 nmol HRP were reacted in 400 microL buffer (100 mM NaCl, 25 mM NaHCO$_3$, pH 9.5) for 3 h at 30 C. Then, 30 nmol Anti-Mouse F(ab)$_2$ antibody in 80 microL water was added, and the reaction was continued for additional 90 min at 40 C. The reaction mixture was quenched by addition of 50 microL 0.165M cystein for 30 min and the product was purified on superdex 200 in 100 mM NaCl, 10 mM HEPES pH 7.2. The eluded product was a conjugate of Dextran with anti-FITC and HRP (Dex/anti-FITC/HRP Ratio=1/2/9).

1.12. Anti-FITC-Dex70-HRP (D17030)

10 nmol divinylsulphone activated 70 kDA MW dextran; 440 nmol HRP and 25 nmol F(ab)$_2$ anti-FITC were reacted in 374 microL buffer (100 mM NaCl, 25 mM NaHCO$_3$, pH 9.5) for 16 at 30 C. The reaction mixture was quenched by addition of 50 microL 0.165M cystein for 30 min and the product purified on superdex 200 in 100 mM NaCl, 10 mM HEPES pH 7.2. The eluded product was a Dextran conjugate comprising Anti-FITC and HRP (ratio 1:1:1).

Molecules 1.10, 1.11 and 1.12 represent embodiments of antibody-Dextran-HRP conjugates which may be useful as probes for detection of deposited reporter molecules. Conjugate 1.10. may also be useful as a further probe for the detection of the probes bound to the deposited reporter (e.g. on step (b) of the method for detecting a marker in the target site described above).

3. Example of IHC Stainings Using the Method of the Invention

IHC was carried out on formalin fixed paraffin embedded tonsils. 3-5 micron sections were cut, baked and stored at 4 C, until used. Paraffin was then removed by xylene (2×5 min); 99% ethanol (2×2 min); 70% ethanol (2×2 min) and finally water. The slides were put in the target retrieval solution, pH 9, (DAKO S2367) then heated in microwave oven (boiled for 10 min). Afterwards, the slides were allowed to cool and then were transferred to the wash buffer (DAKO S3006). The procedure was followed by a step of blocking of endogenous Peroxides activity with 3% hydrogen peroxide for 5 min., then again the slides were transferred into the wash buffer and then stained. To minimize slide to slide variation each comparative experiment was carried out with consecutively cut sections during the same day. The specific as well as background signals were scored using a score scale from 0 to 4 wherein 0 is representing no stain at all, 1—weakly stained, 2—moderately stained, 3—strongly stained, 4—over stained.

IHC Experiment 1.

Cytokeratin, Goat-anti-Mouse-HRP and Anti-FITC-HRP each were diluted in 2% BSA, 0.2% Casein, 2% PEG, 0.1% Tween20, 0.1 M NaCL, 10 mM HEPES pH 7.2. (BCPT-buffer). Reporter D17128 and DAB (DAKO K5007 C) were diluted in DAB substrate buffer (DAKO K5007 B). All incubations lasted 5 min, followed by 2 min wash in DAKO washing buffer S3006, except for after the incubation with 017128, where washes were performed in 10 mM CHES pH 9+0.1% Tween20.

Table and text below summarize the embodiments of the experiment:

|  | Primary antibody probe | Secondary antibody probe | Cross-linker and reporter | Reporter detection probe | Cross-linker and reporter | Reporter detection probe | Developing solution |
|---|---|---|---|---|---|---|---|
| Slide 1 | Cytokeratin (DAKO M5315) 15 nM | GeM-HRP, D18033, 125 nM, | DAB (DAKO K5007 C) No reporter |  |  |  |  |
| Slide 4 | As slide 1 | GaM-HRP, D18033 5 nM | D17128 100 nM + DAB 1:150 | D17030 50 nM | DAB |  |  |
| Slide 7 | As slide 1 | GaM-HRP, D18033 0.5 nM | As slide 4 | As slide 4 | D17128 100 nM + DAB 1:150 | D17030 50 nM | DAB |
| Slide 9 | As slide 1 | GaM-HRP, D18033 0.5 nM | D17128 20 nM + DAB 1:150 | As slide 4 | As slide 7 | As slide 7 | ☐AB |

Slide 1—standard DAB-HRP staining (no amplification), Standard DAB DAKO reagent (K7005 C) contains 3 mM DAB.

Slide 4—deposition of reporter D17128 in the presence of 1 mM DAB—GaM-HRP conjugate D18033 diluted 25 times compared to slide 1—one step amplification Slide 7 and Slide 9—further dilution of GaM-HRP conjugate D18033 compared to slide 1 and additional step of reporter deposition.

Slides 1, 4 and 7 were all specifically stained scoring from 2.5 to 3. A 250 times amplification of the signal (slide 9 compared to slide 1) was achieved due to deposition of reporter D17128 in the presence of DAB followed by recognition the reporter by Anti-FITC-HRP probe D17030. Remarkably the stains of both slides 7 and 9 remained crisp (i.e. non-diffused), with sharp borders between stained and unstained areas indicating that very little diffusion takes place in the deposition sites.

IHC Experiment 2.

Cytokeratin, GaM-HRP and Anti-FITC-HRP were all diluted in 2% BSA, 0.2% Casein, 2% PEG, 0.1% Tween20, 0.1 M NaCL, 10 mM HEPES, pH 7.2. (BCPT-buffer). D17128 and DAB (DAKO K5007 C) were diluted in DAB substrate buffer (DAKO K5007 B). All incubations were 5 min, followed by 2 min wash in DAKO S3006, except following the incubation with reporter D17128, wherein the washes were performed in 10 mM CHES pH 9+0.1% Tween20.

The table and text below summarize the embodiments of the experiment:

|  | Primary & secondary antibody probes | Cross-linker & reporter | Reporter probe | Developing solution |
|---|---|---|---|---|
| Slide 9 | Cytokeratin DAKO M5315 15 nM + GaM-HRP D18033 10 nM | D17128 25 nM no cross-linker | D18058 Anti-FITC-HRP 25 nM | DAB (DAKO K5007 C) |
| Slide 12 | As slide 9 | D17128 25 nM + D17140 100 microM | As slide 9 | DAB (DAKO K5007 C) |
| Slide 14 | As slide 9 | D17128 25 nM + DAB 1:150 | As slide 9 | DAB (DAKO K5007 C) |

Slides 12 and 14 were strongly and specifically stained (both scoring 2), whereas slide 9 was not stained (score 0). The results show that the reporter is not precipitated by HRP in the media without a cross-linker (e.g. DAB (slide 14) or D17140 (slide 12)).

The experiment further illustrates the possibility of reducing the number of steps by pre-incubating (for 10 min) primary antibody with secondary antibody-HRP conjugate.
IHC Experiment 3.

Cytokeratin, GaM-HRP and Anti-FITC-HRP each were diluted in 2% BSA, 0.2% Casein, 2% PEG, 0.1% Tween20, 0.1 M NaCL, 10 mM HEPES, pH 7.2. (BCPT-buffer). D17128 and DAB (DAKO K5007 C) were diluted in DAB substrate buffer (DAKO K5007 B). All incubations were 5 min, followed by 2 min wash in DAKO S3006, except following the incubation with D17128 and D18044, wherein washes were performed in 10 mM CHES pH 9+0.1% Tween20. When the third step of incubation of the slides with DAB in substrate buffer was applied (slides 3 and 5), the incubation time was 1 min.

The table and text below summarize the embodiments of the experiment:

accordance with the results obtained in IHC experiment 2 (described above). On slide 5, where DAB was applied prior to application of the reporter conjugate D17128, a staining was observed (score 2), albeit not quite as intense as on slide 3.

This results show that a cross-linker can be first applied in a separate step before incubating the slide with both reporter and cross-linker (i.e. on pre-incubation step). Another positive effect of applying DAB prior to depositing the labeled reporter observed was a remarkable reduction of the background staining (scored 0.5-1 on slide 2, and scored 0 on slide 3), while specific signals intensity did not decrease much, Particularly weak diffuse background staining associated with unspecific binding of Goat-anti-Mouse-HRP conjugates, was in many cases virtually eliminated by the 1 min extra DAB step prior to deposition.
IHC Experiment 4.

Cytokeratin, GaM-HRP and Anti-FITC-HRP were all diluted in 2% BSA, 0.2% Casein, 2% PEG, 0.1% Tween20, 0.1 M NaCL, 10 mM HEPES, pH 7.2. (BCPT-buffer). D17128, D18044 and DAB (DAKO K5007 C) were diluted in DAB substrate buffer (DAKO K5007 B). All incubations were 5 min, followed by 2 min wash in DAKO S3006, except following incubations with D17128 and D18044, wherein washes were performed in 10 mM CHES pH 9+0.1% Tween20.

The table and text below summarize the embodiments of the experiment:

|  | Primary antibody probe | Secondary antibody probes | Cross-linker and reporter | Cross-linker and reporter | Reporter probe | Developing solution |
|---|---|---|---|---|---|---|
| Slide 2 | Cytokeratin DAKO M5315 15 nM | GAM-HRP, D18033 3 nM | D17128 50 nM + DAB 1:150 | D18058 Anti-FITC-HRP 50 nM |  | DAB |
| Slide 3 | As slide 2 | As slide 2 | DAB No reporter | D17128 50 nM A-DAB 1:150 | D18058 Anti-FITC-HRP 50 nM | DAB |
| Slide 4 | As slide 2 | As slide 2 | D17128 50 nM No cross-linker | D18058 Anti-F ITC-HRP 50 nM |  | DAB |
| Slide 5 | As slide 2 | As slide 2 | DAB No reporter | D17128 50 nM No cross-linker | D18058 Anti-FITC-HRP 50 nM | DAB |

Slide 2 was the most intensely stained slide (score 3), showing that the one minute of extra application of DAB of the third step on slide 3 (score 2,5) did not much improve, but rather slightly reduced the staining intensity. The lack of staining in absence of cross-linker on slide 4 (score 0) is in

|  | Primary &secondary antibody probes | Preincubation with cross-linker (DAB) | Cross-linker (DAB) & reporter | | |
| --- | --- | --- | --- | --- | --- |
| Slide 8 | Cytokeratin DAKO M5315 15 nM + GaM-HRP D18033 10 nM | DAB 1:50 in substrate buffer (DAKO K5007 C), 1 min. | D17128 50 nM + DAB 1:50 (DAKO K5007 C) | 50 nM D 18058 | DAB |
| Slide 9 | As slide 8 | As slide 8 | D17128 50 nM + DAB 1:150 | As slide 8 | As slide 8 |
| Slide 10 | As slide 8 | As slide 8 | D17128 50 nM + DAB 1:500 | As slide 8 | As slide 8 |
| Slide 11 | As slide 8 | As slide 8 | D 18044 5 microM + DAB 1:50 | As slide 8 | As slide 8 |
| Slide 12 | As slide 8 | As slide 8 | D18044 5 microM + DAB 1:150 | As slide 8 | As slide 8 |
| Slide 13 | As slide 8 | As slide 8 | D18044 5 microM + DAB 1:500 | As slide 8 | As slide 8 |

This experiment illustrates the effect of cross linker concentration on deposition of two different types of reporters. Slide 9 was the most intensely stained slide (score 4). DAB as cross linker was applied on slide 9 at dilution 1:150, (1 mM). A higher (1:50 (3 mM), slide 8) or lower (1:500 (0.3 mM), slide 10) concentrations of DAB gave slightly less intense staining (score 3.5). The background reducing effect of the pre-incubation with DAB was also visible; none of the six slides (of the above table) had significant background staining.

The low molecular weight reporters (e.g. reporter 18044 described above) were better deposited at lower concentrations of DAB (slide 13; score 3); the staining intensity decreased with increasing DAB concentrations (slide 12, score 2.5; slide 11, score 2).

This experiment also illustrates that larger reporter molecules comprising many peroxidase substrate moieties can be used at lower amounts (e.g. Fluorescein-Ferulic Acid Dextran conjugate D17128, 50 nM) compared to smaller reporter molecules comprising the same but fewer peroxidase substrate moieties (e.g. D 18044, t 5 microM) to achieve the same or even better staining results.

4. Example of Amplification of a Nucleic Acid Probe Signal Using the Method of the Invention By running samples with and without the use of DAB in the Chromogen solution and the signal enhancer solution the precipitating effect of DAB can be illustrated. Further illustration of the inventions signal amplification can be obtained by further dilution of either the probe, the antibody or by omitting the second Peroxidase-blocking step.

Tissue: Formalin-fixed Paraffin embedded Tonsil.
Fluorescein labeled probe targeted against the centromer of Chromosome 11.
The Following Solutions are Used in the Example:

| | |
| --- | --- |
| Antigen retrieval/pre-treatment | (Dako K 5599) |
| Washbuffer1 | (Dako K 5331) |
| Washbuffer2 | (Dako S 3006) |
| Pepsin RTU | (Dako K 5331) |
| Stringent washbuffer, | (Dako K 5331) |

-continued

| | |
| --- | --- |
| R-a-Fitc/HRP, F(ab) | (Dako P 5100) |
| Antibody diluent | (Dako S 2022) |
| Probe | (Dako Y 5505) |
| Peroxidase-Blocking solution | (Dako S 2023) |
| Nuclear Fast red | (Dako S1968) |
| Chromogen buffer | (Dako K5007) |

A Hybridizer(Dako S2451) was used for hybridising the probes

Preparation of the Chromogen Solution and the Signal Enhancer Solution:

Solution A:
102.5 mg 5-amino-2[3-[5-amino-1,3-dihydro-3,3-dimethyl-1-(4sulfobutyl)-2H indol-2-ylidene]-1-propenyl]-3, 3dimethyl-1-(4sulfobutyl)-3H-Indolium, ter trifluoroacetate is dissolved in 4,525 mL Propanediol/water 8:2

Solution B:
59.6 mg 3,3'-Di-aminoberizidine dihydrochloride is dissolved 5.96 mL Propanediol/water 8:2 13.7 µL. 12 M Hydrochloric acid is added.

Solution C:
Solution A and Solution B are mixed in the ratio 1 mL A:9 mL B.

Chromogen Solution:
For staining these stock solutions were diluted into the chromogen buffer of kits obtained from Dakocytomation code # K5007.
1 mL Solution C is mixed with 19 mL Chromogen buffer Solution D:
1 mL Solution B is diluted with 499 mL Chromogen buffer.

Signal Enhancer Solution:
This is a solution of D1734 in 20% ethanol, 0.1 M NaCl, 10 mM CHES pH 9.0 diluted with Solution D to a concentration of 250 nM or 50 nM of Fer-L30-FITC. In the case of No DAB in the solution dilution was performed directly in Chromogen buffer.

Procedure for Tissue Staining:
Human Tonsil tissue slides were de-paraffinized, washed and antigen retrieval was performed in 10 min in a microwave oven. After another wash, pepsin treatment at 37° C. and washing, slides where dehydrated and incubated with the PNA probe. After 5 min denaturing of the sample at 85° C., the probes where hybridized for 1 hour at 45° C. The slides were stringent washed at 65° C. for 10 min. Peroxidase was blocked for 3 min, the slides were washed and incubated with an Rabbit-anti-FITC/HRP diluted 1:20. After 30 min the slides where washed and incubated with the signal enhancer solution. After 30 min the slides where washed, peroxidase was blocked for 3 min, washed again and the slides were incubated with an Rabbit-anti-FITC/HRP diluted 1/20. After 30 min the slides were washed and incubated with a Chromogen solution. Following washing with water the slides were counterstained with nuclear fast red, washed and mounted.

The experimental set-up and results of the staining are illustrated in the following table:

| Slide #. | Probe 1 time | anti-FITC/HRP Antiboby 30 min | Signal enhancer solution 30 min | anti-FITC/HRP Antiboby 30 min | Signal-intensity | Comments |
|---|---|---|---|---|---|---|
| 1 | Buffer | Anti FITC/HRP 1:50 | $Fer_6$-$Flu_3$ 50 nM with DAB | 1:20 | 0 | |
| 2 | Y5505 Diluted 10 X | 1:100 | $Fer_6$-$Flu_3$ 50 nM | 1:20 | 0 | |
| 3 | Y5505 Fortyndet 50 x | 1:100 | $Fer_6$-$Flu_3$ 50 nM with DAB | 1:20 | 1½ | No DAB in the chromogen solution |
| 4 | Y5505 Diluted 10 x | 1:100 | $Fer_6$-$Flu_3$ 50 nM with DAB | 1:20 | 2½ | |
| 5 | Y5505 Diluted 10 x | 1:100 | $Fer_6$-$Flu_3$ 250 nM with DAB | 1:20 | 4 | Over stained/ to much signal |
| 6 | Y5505 Diluted 10 x | 1:100 | $Fer_6$-$Flu_3$ 250 nM | 1:20 | 0½ | |
| 7 | Y5505 Fortyndet 10 x | 1:100 | No amplification stained directly after first incubation with anti FITC/HRP | | 0 | |

Slide 1 is a control showing probe is need to get a signal.

Slide 2 shows that without a cross-linker in the signal enhancing solution no specific signal is obtained.

Slide 3 shows that adding a cross-linker (DAB) to the signal enhancing solution results in high signal amplification. This is the only slide that did not have DAB in the chromogen solution.

Slide 4 shows that adding a cross-linker to the chromogen solution further enhances the signal (compared to slide 3).

Slide 6 shows that by increasing the concentration of the signal enhancer (D17134) a weak signal can be obtained without a crosslinker. However adding a cross-linker gives a strong amplification of this signal (as illustrated by slide 5).

The invention claimed is:

1. A method of detecting of a biological marker in a biological sample in vitro, comprising the following steps:
  a) incubating a biological sample presumably comprising a biological marker with one or more probes capable of specifically binding to the biological marker, wherein at least one of said one or more probes comprises at least one moiety of horse radish peroxidase (HRP) and a member of a specific binding pair or a conjugate comprising a member of a specific binding pair, wherein said member of a specific binding pair is capable of specifically binding to the biological marker, thereby forming a complex of the biological marker with the at least one probe;
  b) incubating the sample comprising the complex of (a) in a water solution, the water solution comprising 3,3'-diaminobenzidine, a peroxide compound and a conjugate molecule comprising a combination of different detectable labels, wherein the combination comprises a hapten and a substrate of horse radish peroxidase, thereby depositing said conjugate molecule in a site of the sample where said complex is present; and
  c) detecting the deposited conjugate molecules of (b) and thereby detecting the biological marker.

2. The method according to claim 1, wherein the biological marker is a biological molecule selected from the group consisting of proteins, nucleic acids, lipids, carbohydrates, a molecular complex and a cellular structure.

3. The method according to claim 1, wherein the 3,3'-diaminobenzidine is present in an amount from about 0.3 mM to about 3 mM.

4. The method according to claim 1, wherein the method comprises an additional step between step (a) and step (b), wherein the sample is incubated in a water solution comprising 3,3'-diaminobenzidine in an amount from 0.3 mM to 3 mM and a peroxide compound.

5. The method according to claim 1, wherein step (c) comprises incubating the sample with a substance which is capable of specifically binding to the deposited conjugate.

6. The method according to claim 5, wherein the substance is detectably labeled.

7. The method according to claim 6, wherein the substance is an antibody or a nucleic acid.

8. The method according to claim 7, wherein the method is performed in a format of an immunohistochemistry or in situ hybridization assay.

9. The method according to claim 1, wherein the combination of different detectable labels comprises ferulic acid and/or tyrosine.

10. The method according to claim 1, wherein the combination of different detectable labels comprises ferulic acid.

11. The method according to claim 1, wherein the combination of different detectable labels comprises fluorescein.

12. The method according to claim 1, wherein the member of a specific binding pair is an antibody or a nucleic acid.

* * * * *